United States Patent
Liu et al.

(10) Patent No.: US 9,642,865 B2
(45) Date of Patent: May 9, 2017

(54) ANGIOGENESIS INHIBITORS

(71) Applicant: THE JOHNS HOPKINS UNIVERSITY, Baltimore, MD (US)

(72) Inventors: Jun Liu, Clarksville, MD (US); Curtis Chong, Baltimore, MD (US); David J. Sullivan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/530,398

(22) Filed: Oct. 31, 2014

(65) Prior Publication Data

US 2015/0056267 A1 Feb. 26, 2015

Related U.S. Application Data

(63) Continuation of application No. 13/627,939, filed on Sep. 26, 2012, now abandoned, which is a continuation of application No. 11/630,596, filed as application No. PCT/US2005/023015 on Jun. 27, 2005, now Pat. No. 8,980,930.

(Continued)

(51) Int. Cl.
| | |
|---|---|
| A61K 31/58 | (2006.01) |
| A61K 31/00 | (2006.01) |
| A61K 31/365 | (2006.01) |
| A61K 31/4164 | (2006.01) |
| A61K 31/4196 | (2006.01) |
| A61K 31/47 | (2006.01) |
| A61K 31/496 | (2006.01) |
| A61K 31/7072 | (2006.01) |
| A61K 38/50 | (2006.01) |

(Continued)

(52) U.S. Cl.
CPC ............ *A61K 31/58* (2013.01); *A61F 9/0008* (2013.01); *A61F 9/0017* (2013.01); *A61K 31/00* (2013.01); *A61K 31/365* (2013.01); *A61K 31/4164* (2013.01); *A61K 31/4196* (2013.01); *A61K 31/47* (2013.01); *A61K 31/496* (2013.01); *A61K 31/7072* (2013.01); *A61K 38/50* (2013.01); *A61K 45/06* (2013.01)

(58) Field of Classification Search
CPC ..................................................... A61K 31/58
See application file for complete search history.

(56) References Cited

U.S. PATENT DOCUMENTS

| | | |
|---|---|---|
| 5,340,805 A | 8/1994 | Harrington, Jr. |
| 5,405,837 A | 4/1995 | Weber |

(Continued)

FOREIGN PATENT DOCUMENTS

| | | |
|---|---|---|
| BE | 1004029 A6 | 9/1992 |
| CA | 2014202 | 10/1990 |

(Continued)

OTHER PUBLICATIONS

Bell (Arch Ophthalmol, vol. 107, 1989, p. 796).*

(Continued)

*Primary Examiner* — Benjamin Packard
(74) *Attorney, Agent, or Firm* — DLA Piper LLP (US)

(57) ABSTRACT

Described herein are methods of inhibiting angiogenesis, and treating or preventing a disease or disorder (or symptoms thereof) associated with angiogenesis, wherein an anti-angiogenesis compound is administered to a subject.

19 Claims, 9 Drawing Sheets

TABLE 1: IC50 values for compounds identified by JHCCSI

| | IC$_{50}$ HUVEC (nM) | IC$_{50}$ RKO (nM) | IC$_{50}$ Fibroblast (nM) | Peak plasma level (nM) |
|---|---|---|---|---|
| Trifluridine (anti-viral used to treat herpes simplex keratitis) | 299 ± 53 | > 10,000 | > 10,000 | N/A: Opthalmic anti-viral that penetrates to retina |
| Mycophenolic Acid (inosine monophosphate dehydrogenase inhibitor) | 99 ± 17 | 131 ± 8, 128 ± 6, Jurkat T-cells | 422 ± 24 | 76,500 |
| Danazol (pituitary suppressant used to treat endometriosis) | 483 ± 66 | > 100,000 | > 100,000 | ~800 |
| Asparaginase (converts asparagine to ammonia and aspartate used to treat leukemia) | 1 U/mL ± 0.1 | 2.4 U/mL ± 0.2, 3 U/mL ± 0.15, Jurkat T-cell | > 500 U/mL | > 27 U/mL |
| Itraconazole (inhibits steroid biosynthesis; used to treat fungal infections) | 261 ± 24 | Pending | > 100,000 | 3,233 |

Related U.S. Application Data

(60) Provisional application No. 60/583,076, filed on Jun. 25, 2004.

(51) Int. Cl.
  *A61F 9/00* (2006.01)
  *A61K 45/06* (2006.01)

(56) References Cited

U.S. PATENT DOCUMENTS

| | | | |
|---|---|---|---|
| 5,633,274 A | 5/1997 | Halperin et al. | |
| 5,688,529 A | 11/1997 | Lidgate et al. | |
| 5,688,765 A * | 11/1997 | Sullivan | A61K 31/565 514/20.8 |
| 5,780,676 A | 7/1998 | Boehm et al. | |
| 6,114,355 A * | 9/2000 | D'Amato | A61K 31/19 514/323 |
| 8,227,457 B2 | 7/2012 | Bar-Or | |
| 2001/0041706 A1 | 11/2001 | Synold | |
| 2002/0042401 A1 | 4/2002 | Ferguson | |
| 2003/0195177 A1 | 10/2003 | Leonard | |
| 2004/0067985 A1 | 4/2004 | Haviv et al. | |
| 2004/0092740 A1 | 5/2004 | Dumas et al. | |
| 2007/0111972 A1 | 5/2007 | Bar-Or | |
| 2007/0179152 A1 | 8/2007 | Lee et al. | |

FOREIGN PATENT DOCUMENTS

| | | |
|---|---|---|
| CA | 2 074 216 A1 | 1/1993 |
| CA | 2 118 313 A1 | 9/1994 |
| CA | 2263077 | 2/1998 |
| CA | 2295035 | 12/1998 |
| CA | 2 356 462 A1 | 7/2000 |
| EP | 0 661 054 | 7/1995 |
| WO | WO 96/29325 A1 | 9/1996 |
| WO | WO 99/20271 A1 | 4/1999 |
| WO | WO-02/46171 | 6/2002 |
| WO | WO-02/055018 | 7/2002 |
| WO | WO 03/092617 A2 | 11/2003 |
| WO | WO 2004/012746 A2 | 2/2004 |
| WO | WO-2004/039330 A2 | 5/2004 |
| WO | WO 2004/105696 A2 | 12/2004 |
| WO | WO 2005/000208 A2 | 1/2005 |

OTHER PUBLICATIONS

Zarn et al., "Azole Fungicides Affect Mammalian Steroidogenesis by inhibiting Sterol 14α-Demethylase and Aromatase", *Environmental Health Perspectives* 111(3):255-261, 2003.
Aftab et. al., "Itraconazole inhibits angiogenesis and tumor growth in non-small cell lung cancer", *Cancer Research*, 2011.
Chong et al., "Inhibition of Angiogenesis by the Antifungal Drug Itraconazole", *ACS Chem. Biol.* V2, 263, 2007.
2011 *ASCO Meeting*: A noncomparative randomized phase II study of two dose levels of itraconazole in men with metastatic castration-resistant prostate cancer (mCRPC): A DOD/PCCTC trial.
Folkman et al., Angiogenesis Inhibition and Tumor Regression Caused by Heparin or a Heparin Fragment in the Presence of Cortisone, *Science* 221(4612):719-725, 1983.
Presta et al., Heparin derivatives as angiogenesis inhibitors, *Curr. Pharm. Des.* 2003:9(7):553-566.
Pisano et al., "Undersulfated, low-molecular-weight glycol-split heparin as an antiangiogenic VEGF antagonist", *Glycobiology* 15(2):1C-6C, 2005.
Dhar et al., "A modified approach to 2-(N-aryl)-1,3-oxazoles: application to the synthesis of the IMPDH inhibitor BMS-337197 and analogues", *Org. Lett.*, 4(12):2091-3 (2002).
Jain et al., "Characterization of pharmacological efficacy of VX-148, a new, potent immunosuppressive inosine 5'-monophosphate dehydrogenase inhibitor", *J. Pharmacol. Exp. Ther.*, 302(3):1272-7 (2002).
Jain et al., "VX-944: A Specific, Reversible IMPDH Inhibitor with Potent Anti-Proliferative Effects in Human Tumor Cell Lines Derived from Hematological Malignancies", *Blood*, 100(11): Abstract No. 2248 (2002).
Ren et al., "Immunotherapy of Chronic Hepatitis B by Hepatitis B Vaccine: Induction of T Cell Proliferative Response Specific for Envelope Proteins and Predominant TH1 Pathway", *Hepatology*, AASLD Abstracts, vol. 34, No. 4, Pt. 2, p. 633A, abstract No. 1846 (2001).
BE 1004029 translation via EPO (specification and claims) machine translated Dec. 15, 2011.
Kerbel, R.S.: "Tumor angiogenesis"; N Engl J Med 358;19 (2008) 2039-2049.
European Search Report for Corresponding European Application No. 05787846.4 dated Feb. 2, 2010.
Zhi-Hong, Liu et al.: "Mycophenolate Mofetil: An Inhibitor of Angiogenesis, Cell Migration and Proliferation of Endothelial Cells", Journal of American Society of Nephrology, vol. 11, No. Special Issue, Sep. 1, 2000, p. 90A, XP009128314.
Database WPI Week 200275, Thomson Scientific, London, GB; AN 2002-694921, XP002564729, Aug. 28, 2002.
Baltatzis et al., "Mycophenolate Mofetil as an Immunomodulatory Agent in the Treatment of Chronic Ocular Inflammatory Disorders", *Opthamology*, 110(5):1061-1064 (2003).
Zam et al., "Azole Fungicides Affect Mammalian Steroidogenesis by Inhibiting Sterol 14a-Demethylase and Aromatase", Environmental Health Perspectives 111(3):255-261, 2003.
Bajou et al.: *Human Breast Adenocarcinoma Cell Lines Promote Angiogenesis by Providing Cells With uPA-PAI-1 and by Enhancing Their Expression*; Int. J. Cancer: 100, 501-506 (2002).
Peters et al: *Danazol Therapy in Hormone-Sensitive Mammary Carcinoma*; Cancer 40:2797-2800, 1977.

* cited by examiner

Figure 1

TABLE 1: IC50 values for compounds identified by JHCCSI

| | $IC_{50}$ HUVEC (nM) | $IC_{50}$ RKO (nM) | $IC_{50}$ Fibroblast (nM) | Peak plasma level (nM) |
|---|---|---|---|---|
| 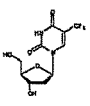 Trifluridine (anti-viral used to treat herpes simplex keratitis) | 299 ± 53 | > 10,000 | > 10,000 | N/A: Opthalmic anti-viral that penetrates to retina |
| 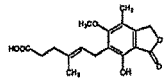 Mycophenolic Acid (inosine monophosphate dehydrogenase inhibitor) | 99 ± 17 | 131 ± 8<br>128 ± 6,<br>Jurkat T-cells | 422 ± 24 | 76,500 |
| 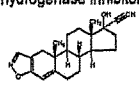 Danazol (pituitary suppressant used to treat endometriosis) | 483 ± 66 | > 100,000 | > 100,000 | ~800 |
| Asparaginase (converts asparagine to ammonia and aspartate used to treat leukemia) | 1 U/mL ± 0.1 | 2.4 U/mL ± 0.2<br>3 U/mL ± 0.15,<br>Jurkat T-cell | > 500 U/mL | > 27 U/mL |
| 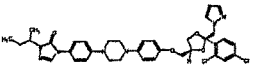 Itraconazole (inhibits steroid biosynthesis; used to treat fungal infections) | 261 ± 24 | Pending | > 100,000 | 3,233 |

Figure 2

Table 2: Structure-activity relationships

| | HUVEC | HFF | Jurkat T-cells | RKO |
|---|---|---|---|---|
| Itraconazole | 0.261 (24) | > 100 | > 100 | |
| Miconazole | 2.47 (0.37) | 28.2 (0.6) | 10.8 (0.3) | |
| Sulconazole | 2.6 (0.44) | 35.7 (1.8) | 11.4 (0.56) | |
| Econazole | 4.8 (2.0) | 31.7 (6.3) | 16 (4.6) | |
| Terconazole | 7.1 (1.3) | | > 100 | 8.3 (4) |

| | HUVEC | HFF | Jurkat T-cells | RKO |
|---|---|---|---|---|
| Clotrimazole | 8 (1.3) | 22.1 (1.5) | 7.96 (0.2) | |
| Ketoconazole | 10.4 (3.7) | 19.6 (4.5) | 24.8 (0.4) | |
| Bifonazole | 11.9 (3.9) | 29.1 (8.5) | 22.2 (0.81) | |
| Fluconazole | > 100 | > 100 | > 100 | |
| Voriconazole | > 100 | > 100 | > 100 | |

Figure 3
Endothelial cells
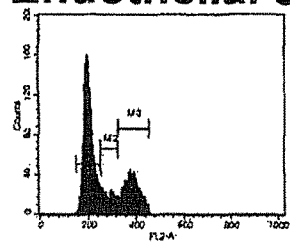
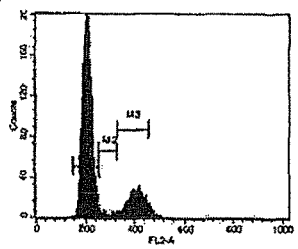
| | Control | Fumagillin (2 nM) |
|---|---|---|
| G1: | 62.5 % | 78.9 % |
| S: | 10.5 % | 2.2 % |
| G2/M: | 27.2 % | 17.7 % |
| | | G1/S Arrest |
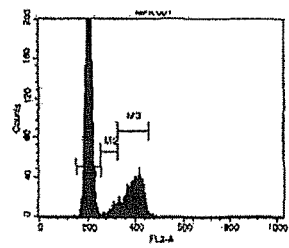
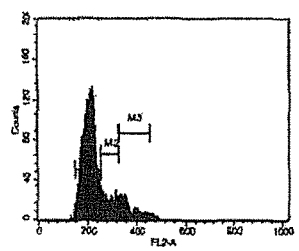
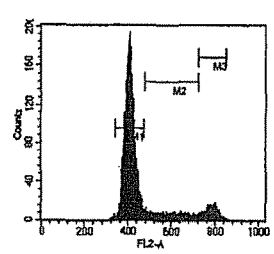
| MFA (1 µM) | Trifluridine (5 µM) | Itraconazole (2.5 µM) |
|---|---|---|
| 70 % | 75 % | 84 % |
| 3.2 % | 13.2 % | 8 % |
| 26.7 % | 11.6 % | 8 % |
| G1/S Arrest | S Arrest | G1/S Arrest |

Figure 3 (continued)
Fibroblast cells
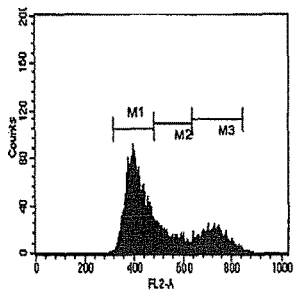 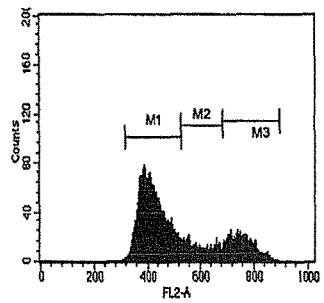 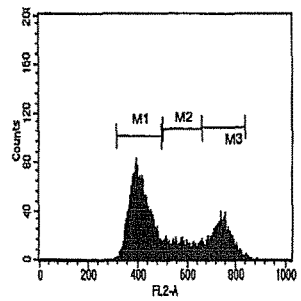
|  | Control | Fumagillin (2 nM) | MFA (3 μM) |
|---|---|---|---|
| G1: | 63 % | 69 % | 60 % |
| S: | 17 % | 13.5 % | 15 % |
| G2/M | 20 % | 17.8 % | 25 % |
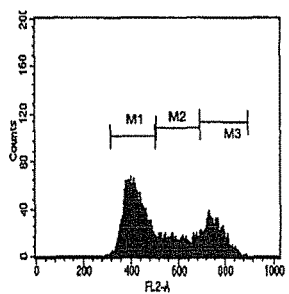 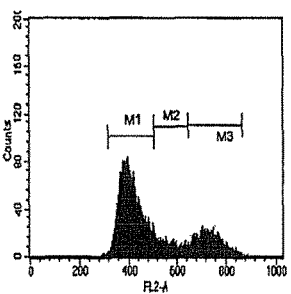
Trifluridine (10 μM)
55 %
20 %
25 %
Itraconazole (10 μM)
68 %
12 %
20 %
Slight G1/S Arrest Figure 5
A
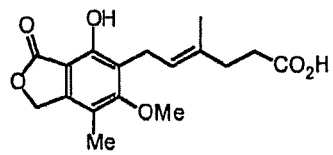
Mycophenolic Acid
B
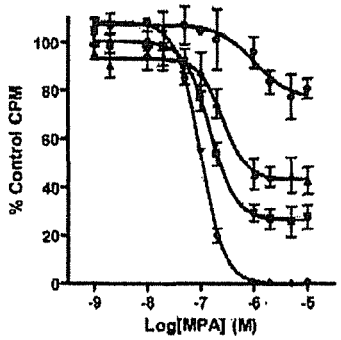
C
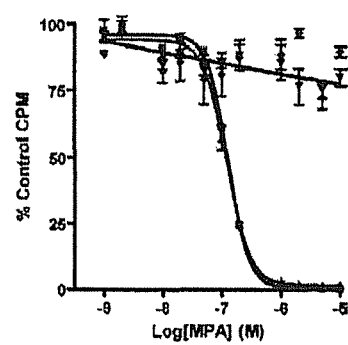
D
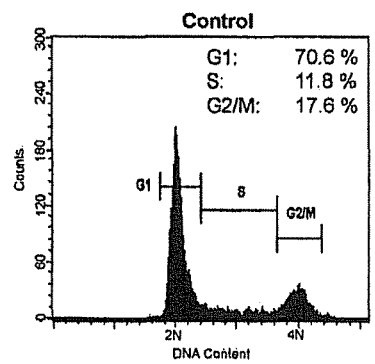
E
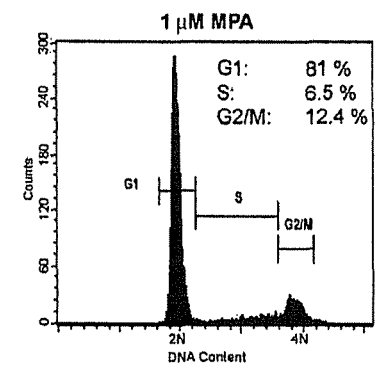
F
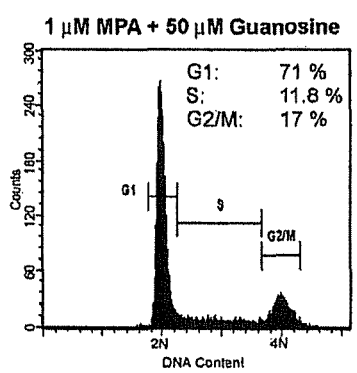

ANGIOGENESIS INHIBITORS

CROSS-REFERENCE TO RELATED APPLICATIONS

This application is a continuation of U.S. Ser. No. 13/627,939, filed Sep. 26, 2012, which is a continuation of U.S. Ser. No. 11/630,596, filed Dec. 17, 2007, which is a 35 U.S.C. §371 National Stage Application of PCT Application No. PCT/US2005/023015, filed Jun. 27, 2005, which claims the benefit under 35 U.S.C. §119(e) to U.S. Provisional Application Ser. No. 60/583,076, filed Jun. 25, 2004. The disclosure of each of the prior applications is considered part of and is incorporated by reference in, the disclosure of this application.

GRANT INFORMATION

This work described herein was supported by a grant from the National Cancer Institute (NCI) (Grant No. CA078743). Therefore, the U.S. Government may have certain rights in the invention.

BACKGROUND OF THE INVENTION

Angiogenesis may be defined as the development of a blood supply to a given area of tissue. The development of a blood supply may be part of normal embryonic development, represent the revascularization of a wound bed, or involve the stimulation of vessel growth by inflammatory or malignant cells. Sometimes angiogenesis is defined as the proliferation of new capillaries from pre-existing blood vessels. New growth of soft tissue requires new vascularization, and the concept of angiogenesis is a key component of tissue growth and in particular, a key point of intervention in pathological tissue growth.

Angiogenesis is a fundamental process necessary for embryonic development, subsequent growth, and tissue repair. Angiogenesis is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g., in the healing of wounds and fractures.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating new blood vessels. Creation of the new microvascular system can initiate or exacerbate disease conditions.

Medical science has recognized that angiogenesis is an important factor in the initiation and/or proliferation of a large number of diverse disease conditions. Under normal physiological conditions, humans and other animals only undergo angiogenesis in very specific, restricted situations. For example, angiogenesis is normally observed in wound healing, fetal and embryonic development, and in the formation of the corpus luteum, endometrium and placenta. The process of angiogenesis has been found to be altered in a number of disease states, and in many instances, the pathological damage associated with the disease is related to uncontrolled angiogenesis. Since it was first put forward over thirty years ago, the hypothesis that angiogenesis is required for tumor growth and metastasis has gained extensive experimental support (Folkman, J. (1971) *N. Engl. J. Med.* 285, 1182-1186, Hanahan, D. & Folkman, J. (1996) *Cell* 86, 353-364). For example, angiogenesis is a factor in tumor growth, since a tumor must continuously stimulate growth of new capillary blood vessels in order to grow. Angiogenesis is an essential part of the growth of human solid cancer, and abnormal angiogenesis is associated with other diseases such as rheumatoid arthritis, psoriasis, and diabetic retinopathy (Folkman, J. and Klagsbrun, M., Science 235:442-447, (1987)). In addition to tumor growth and metastasis, angiogenesis has also been implicated in rheumatoid arthritis, diabetic retinopathy and macular degeneration, suggesting that inhibition of angiogenesis may be useful for the treatment of these disorders (Carmeliet, P. (2003) *Nat. Med.* 9, 653-660).

One way to accelerate the drug discovery process for angiogenesis related disorders/diseases involves finding new uses for existing drugs. Because the toxicity, pharmacokinetics, and clinical properties of existing drugs are well established, compounds that show activity can be rapidly and inexpensively evaluated as new treatments and moved into the clinic if appropriate. Furthermore, the extensive structure/activity data accumulated during the development of each drug can greatly facilitate mechanistic studies for target identification or validation.

Clearly, the development and progress of many disease conditions can be controlled by controlling the process of angiogenesis. However, many materials which appear promising in vitro have proven to be relatively ineffective when applied in vivo. Furthermore, various of such materials have been found to be unstable, toxic, or otherwise difficult to employ. Consequently, there is a need for methods and materials capable of controlling and inhibiting angiogenesis in a reliable manner. It is therefore an object of the invention to provide compounds and pharmaceutical compositions which exhibit activity as inhibitors of angiogenesis.

SUMMARY OF THE INVENTION

In one aspect, the invention provides a method of inhibiting angiogenesis in a subject, the method comprising the step of administering to the subject an effective amount of an anti-angiogenic compound selected from: an IMPDH inhibitor; an imidazole of Formula I; a triazole of Formula II; trifluridine; danazol; and asparaginase.

In another aspect, the invention provides the use of anti-angiogenic compound in the manufacture of a medicament for inhibiting or reducing angiogenesis in a patient, the anti-angiogenic compound being selected from: an IMPDH inhibitor; an imidazole of Formula I; a triazole of Formula II; trifluridine; danazol; and asparaginase.

In yet another aspect, the invention provides a sustained release device for implantation in a patient and sustained release of an anti-angiogenic compound for at least a period of 30 days, wherein the anti-angiogenic compound is selected from: an IMPDH inhibitor; an imidazole of Formula I; a triazole of Formula II; trifluridine; danazol; and asparaginase.

In yet another aspect, the invention provides a sustained release drug device adapted for implantation in or adjacent to the eye of a patient, the drug delivery device comprising: (i) a drug core comprising anti-angiogenic compound being selected from: an IMPDH inhibitor; an imidazole of Formula I; a triazole of Formula II; trifluridine; danazol; and asparaginase; (ii) an impermeable coating disposed about the core that is substantially impermeable to the passage of the anti-angiogenic compound, having one or more openings therein which permit diffusion of the anti-angiogenic compound, and which is substantially insoluble and inert in body fluids and compatible with body tissues; and, optionally, (iii) one or more permeable polymer members or coatings disposed in the flow path of the anti-angiogenic compound through said openings in said impermeable coating, said permeable polymer being permeable to the passage of the anti-angiogenic compound, and which is substantially insoluble and inert in body fluids and compatible with body tissues; wherein the impermeable coating and permeable polymer members or coatings are disposed about the drug core so as to produce, when implanted, a substantially constant rate of release of the anti-angiogenic compound from the device.

In another aspect, the invention provides a sustained release formulation for depot injection in a patient and sustained release of an anti-angiogenic compound for at least a period of 30 days, wherein the formulation includes:

a viscous gel formulation comprising a bioerodible, biocompatible, polymer; and an anti-angiogenic agent dissolved or dispersed therein, which anti-angiogenic agent is selected from: an IMPDH inhibitor; an imidazole of Formula I; a triazole of Formula II; trifluridine; danazol; and asparaginase.

In one embodiment, the invention provides a method, use, device, or formulation, wherein the anti-angiogenic compound is provided in an amount effective for treatment of retinoblastoma, cystoid macular edema (CME), exudative age-related macular degeneration (AMD), diabetic retinopathy, diabetic macular edema, or ocular inflammatory disorders.

In another embodiment, the invention provides a method, use, device, or formulation for treatment of a tumor.

In another embodiment, the invention provides a method, use, device, or formulation for the treatment of dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

In yet another embodiment, the invention provides a method, use, device, or formulation for eliminating or reducing normal but undesired tissue in a patient.

In still another embodiment, the invention provides a method, use, device, or formulation for the reduction of fat.

In a certain embodiment, the invention provides a method, use, device, or formulation, wherein the anti-angiogenic compound is an IMPDH inhibitor.

In a certain embodiment, the invention provides a method, use, device, or formulation, wherein the IMPDH inhibitor has a Ki for inhibiting IMPDH less than about 1 micromolar. In a further embodiment, the invention provides a method, use, device, or formulation, wherein IMPDH inhibitor has a Ki for inhibiting the type II isoform of IMPDH (IMPDH Type II) more than 2 fold greater than the Ki of the inhibitor for inhibiting the type I isoform (IMPDH type I). In a further embodiment, the invention provides a method, use, device, or formulation, wherein the IMPDH inhibitor has a $EC_{50}$ for inhibiting the type II isoform of IMPDH (IMPDH Type II) more than 2 fold greater than the $EC_{50}$ of the inhibitor for inhibiting the type I isoform (IMPDH type I).

In a certain embodiment, the invention provides a method, use, device, or formulation, wherein the IMPDH inhibitor is provided in a dose that produces a serum concentration at least 50 percent less than the inhibitor's EC50 for inhibiting IMPDH in lymphocytes.

In a certain embodiment, the invention provides a method, use, device, or formulation, wherein the IMPDH inhibitor is a mycophenolate. In a further embodiment, the invention provides a method, use, device, or formulation, wherein the mycophenolate is selected from mycophenolic acid and mycophenylate mofetil, or a pharmaceutically acceptable salt or prodrug thereof. In a further embodiment, the invention provides a method, use, device, or formulation, wherein the mycophenolate is an analog of mycophenolic acid having one or more varying substituents at the 2-, 4-, 5-, and 6-positions, or a pharmaceutically acceptable salt or prodrug thereof. In another further embodiment, the invention provides a method, use, device, or formulation, wherein the mycophenolate is a anti-angiogenic metabolite of mycophenolic acid, or a pharmaceutically acceptable salt thereof.

In a certain embodiment, the invention provides a method, use, device, or formulation, wherein the IMPDH inhibitor is selected from: Ribavarin; BMS-337197; VX-497 (merimepodib); VX-148; VX-944; Viramidine; Levovirin; Mizoribine; Mizoribine aglycone; benzamide riboside; selenazofurin; and Tiazofurin or an analog thereof that is anabolized to become an NAD analog that inhibits IMPDH.

In a certain embodiment, the invention provides a method, use, device, or formulation, wherein the IMPDH inhibitor is a nicotinamide adenine dinucleotide (NAD) analog that inhibits IMPDH.

In a certain embodiment, the invention provides a method, use, device, or formulation, wherein the nicotinamide adenine dinucleotide (NAD) analog is 5-ethynyl-1-β-D-ribofuranosylimidazole-4-carboxamide (EICAR) or the methylenebis(phosphonate) analogs C2-MAD and C4-MAD.

In a certain embodiment, the invention provides a method, use, device or formulation, wherein the anti-angiogenic compound inhibits endothelial cell proliferation.

In a certain embodiment, the invention provides a method, use, device or formulation, wherein the anti-angiogenic compound inhibits G1/S cell cycle progression of endothelial cells.

In a certain embodiment, the invention provides a method, use, device or formulation, wherein the anti-angiogenic compound decreases new blood vessel formation.

In another aspect, the invention provides a method of inhibiting or reducing angiogenesis in a subject, the method comprising the step of administering to the subject an angiogenesis-inhibiting compound, wherein the compound is an imidazole compound of formula I:

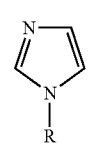

wherein R is selected from:

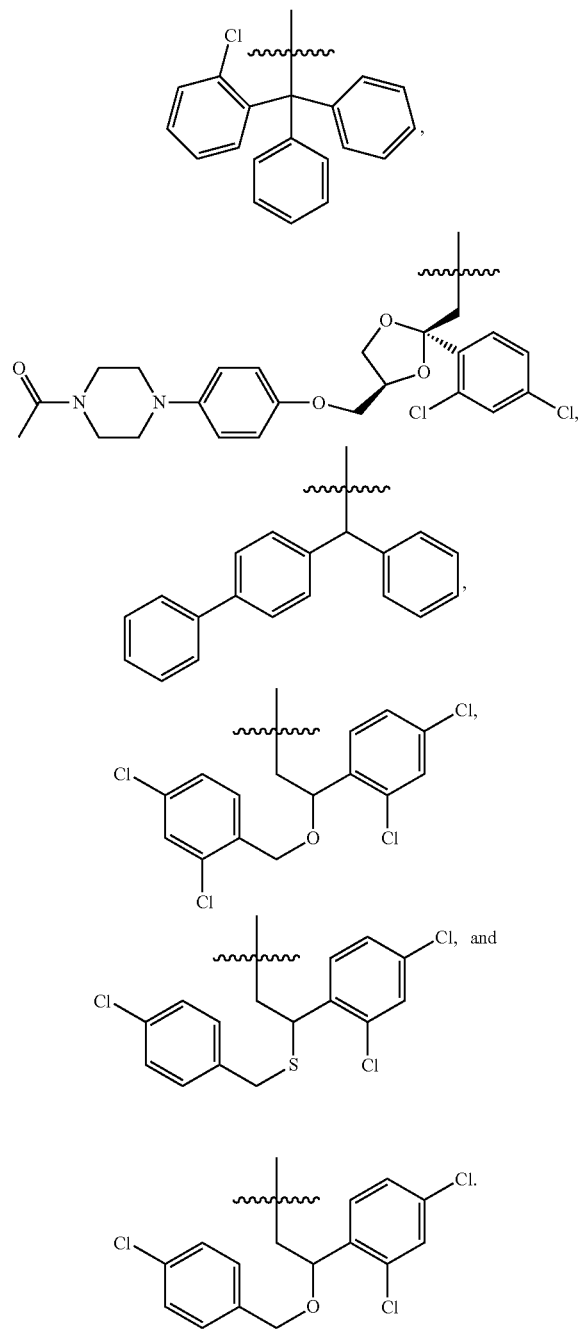

In another aspect, the invention provides a use of anti-angiogenic compound in the manufacture of a medicament for inhibiting or reducing angiogenesis in a patient,
wherein the anti-angiogenic compound is an imidazole compound of formula I:

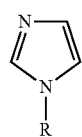

I wherein R is selected from:

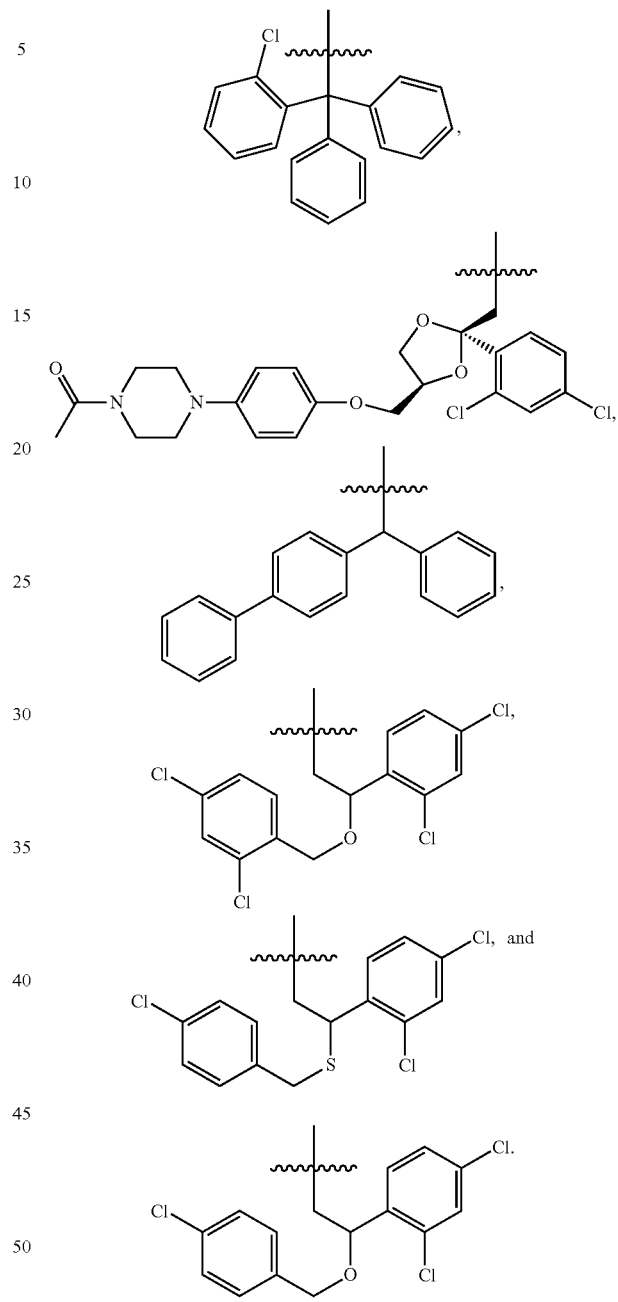

In another aspect, the invention provides a sustained release device for implantation in a patient and sustained release of an anti-angiogenic compound for at least a period of 30 days,
wherein the anti-angiogenic compound is an imidazole compound of formula I:

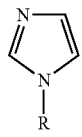

I wherein R is selected from:

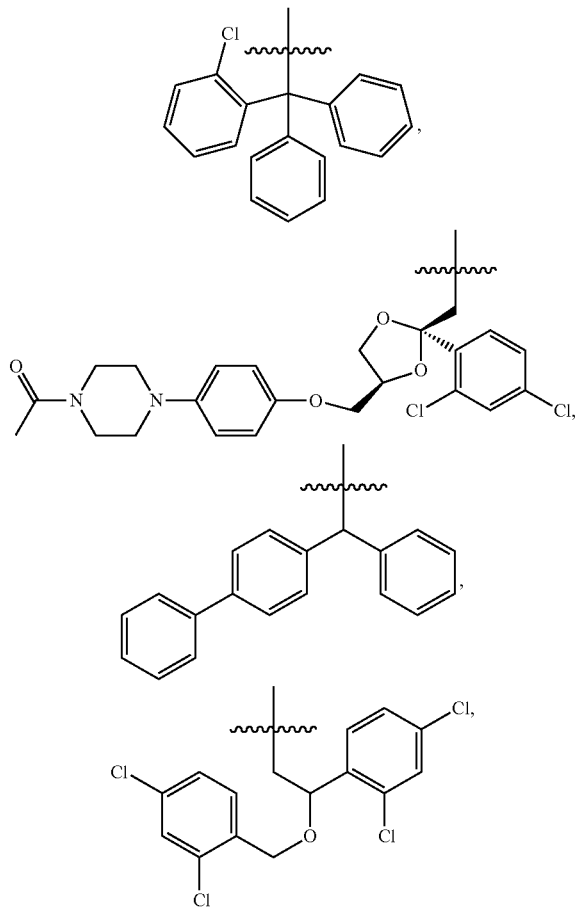

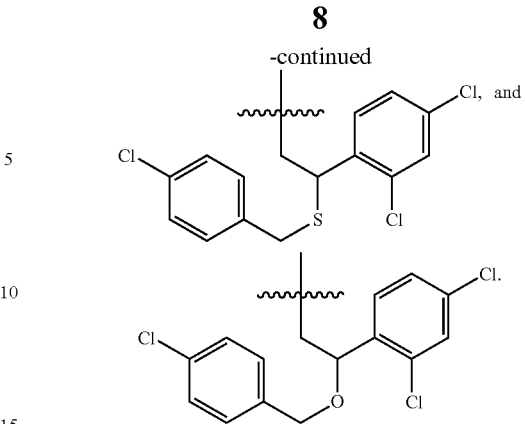

In one embodiment, the invention provides a method, use or device, wherein the imidazole compound is Clotrimazole, Ketoconazole, Bifonazole, Miconazole, Sulconazole, or Econazole.

In another aspect, the invention provides a method of inhibiting or reducing angiogenesis in a subject, the method comprising the step of administering to the subject an angiogenesis-inhibiting compound, wherein the compound is a triazole compound of formula II:

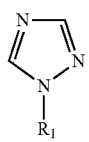

wherein, $R_1$ is

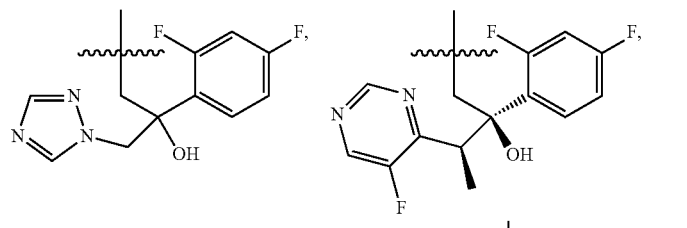

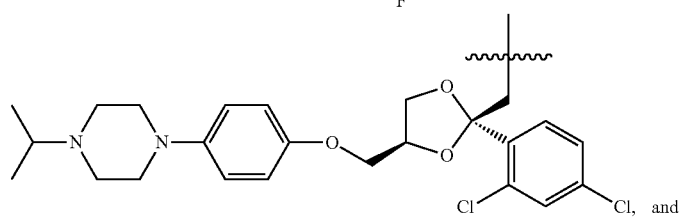

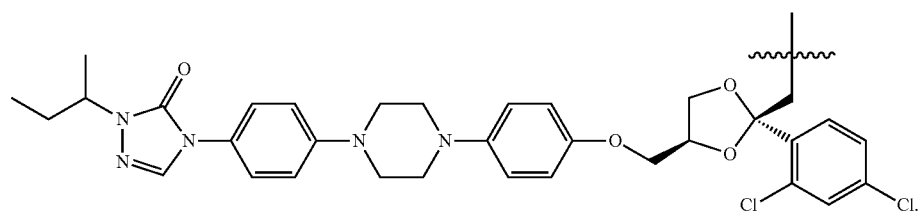

In another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is a triazole compound of formula II:

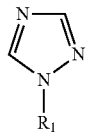

wherein, $R_1$ is

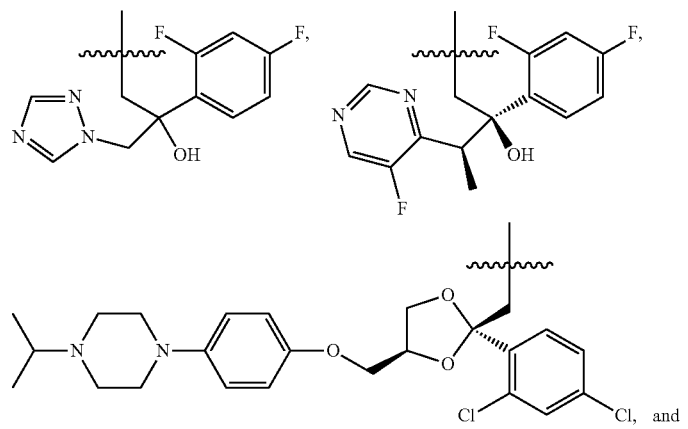

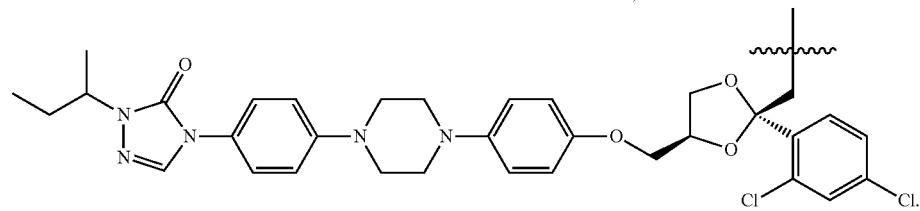

In another aspect, the invention provides a use of an anti-angiogenic compound in the manufacture of a medicament for inhibiting or reducing angiogenesis in a patient, wherein the compound is a triazole compound of formula II:

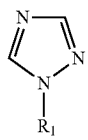

wherein, $R_1$ is

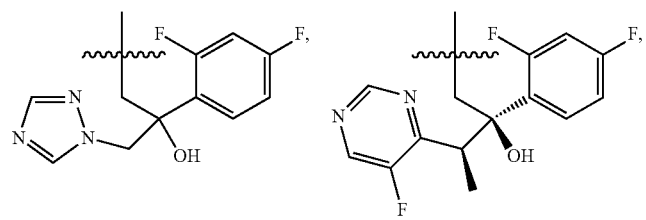

-continued

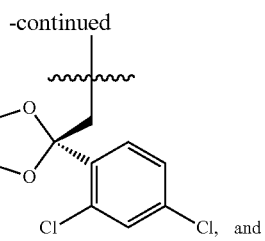

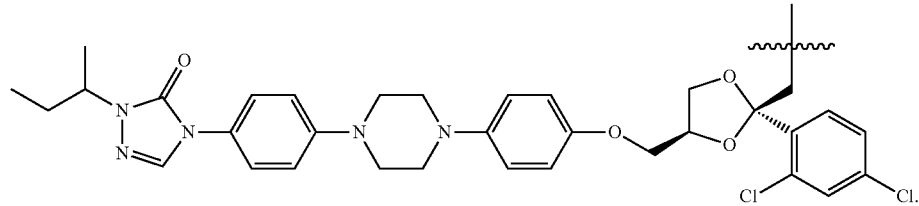

In one embodiment, the invention provides a method or use, wherein the triazole compound is Fluconazol, Voriconazole, Itraconazole, or Terconazole. In another embodiment, the invention provides a method, use, device or formulation, further comprising an additional therapeutic agent.

In a certain embodiment, the invention provides a method, use, device or formulation, wherein the additional therapeutic agent is an angiogenesis-inhibiting compound. In a certain embodiment, the invention provides a method, use, device or formulation, wherein the additional therapeutic agent is an anticancer compound.

In a certain embodiment, the invention provides a method, use, device or formulation, wherein the step of administering the anti-angiogenic compound comprises administering the compound orally, topically, parentally, intravenously or intramuscularly.

In a certain embodiment, the invention provides a method, use, device or formulation, wherein the administration is carried out in a controlled and sustained release.

In a certain embodiment, the invention provides a method, use, device or formulation, wherein the step of administering the anti-angiogenic compound comprises administering the compound in a dosage of between about 0.1 and 100 mg/kg/day.

In a certain embodiment, the invention provides a method, use, device or formulation, wherein the step of administering the anti-angiogenic compound comprises administering the compound in a dosage of less than about 500 mg/day.

In a certain embodiment, the invention provides a method, use, device or formulation, wherein the subject is a human.

In another aspect, the invention provides a kit comprising an effective amount of an anti-angiogenic compound in unit dosage form, together with instructions for administering the anti-angiogenic compound to a subject suffering from or susceptible to a disease or disorder or symptoms thereof associated with angiogenesis.

In one embodiment, the anti-angiogenic compound is MPA.

In a certain embodiment, the invention provides a method, use, device or formulation, comprising the step of administering an effective amount of a composition comprising an anti-angiogenic compound and a pharmaceutically suitable excipient.

In a certain embodiment, the invention provides a method, use, device or formulation of any of the preceding claims, wherein the disease or disorder associated with angiogenesis is selected from: tumor or cancer growth (neoplasia), skin disorders, neovascularization, and inflammatory and arthritic diseases. In a certain embodiment, the disease or disorder associated with angiogenesis is tumor or cancer growth (neoplasia). In a certain embodiment, the disease or disorder is: eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/ens cancer (e.g., gliomas), throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In a certain embodiment, the disease or disorder associated with angiogenesis is a skin disorder. In a certain embodiment, the disease or disorder is: psoriasis, acne, rosacea, warts, eczema, hemangiomas, lymphangiogenesis, Sturge-Weber syndrome, venous ulcers of the skin, neurofibromatosis, and tuberous sclerosis.

In a certain embodiment, the disease or disorder associated with angiogenesis is neovascularization. In certain embodiments, the disease or disorder is: diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardfs disease, pars planitis, chronic retinal detachment, hyperviscosity syndromes, toxoplasmosis, trauma and post-laser complications, and diseases associated with rubeosis (neovascularization of the ankle). In a certain embodiment, the disease or disorder associated with angiogenesis is rheumatoid arthritis, diabetic retinopathy, macular edema, or macular degeneration.

In a certain embodiment, the disease or disorder associated with angiogenesis is inflammatory and arthritic disease. In a certain embodiment, the disease or disorder is: rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In certain embodiments, the subject anti-angiogenic compounds are used as part of a treatment or prevention for an optic neuropathy. The compounds can be administered, for example, by for intraocular injection or implantation. The anti-angiogenic compound can be ad'ministered alone, or in combination with other agents, including anti-inflammatory compounds, neuroprotective agents, agents that reduce introcular pressure (TOP), and/or immunomodulatory compounds. For instance, the anti-angiogenic compound can be administered as part of therapy that includes treatment with a cholinergic agonists, cholinesterase inhibitors, carbonic anhydrase inhibitors, adrenergic agonists (such as alpha2-selective adrenergic agonists), beta-blockers, prostaglandin analogues, osmotic diuretics, p38 kinase antagonists, Cox-2 inhibitors, corticosteroid (such as triamcinolone, dexamethasone, fluocinolone, cortisone, prednisolone, flumetholone, or derivatives thereof such as triamcinolone acetonide or fluocinolone acetonide), salts thereof, isomers thereof, prodrugs thereof, and mixtures of any of these.

As used herein, the terms "optic neuropathy", or "optic neuropathies" are intended to include diseases, disorders, or damage to the nerves or other structures of the eye. By way of example, such optic neuropathies include uveitis, such as anterior uveitis, intermediate uveitis, posterior uveitis, and diffuse uveitis; uveitic syndromes, such as ankylosing spondylitis, juvenile rheumatoid arthritis, pars planitis, toxoplasmosis, cytomegalovirus, inflammation caused by herpes zoster, inflammation caused by herpes simplex, toxocariasis, birdshot chorioretinopathy, presumed ocular histoplasmosis syndrome, syphilis, tuberculosis, Vogt-Koyanagi-Harada syndrome, sympathetic ophthalmia, ocular sarcoidosis and endophthalmitis; masquerade syndromes, such as intraocular malignancy, retinitis pigmentosa, and reactions to drugs; vascular retinopathies, such as hypertensive retinopathy, diabetic retinopathy, central retinal artery occlusion, and central retinal vein occlusion; age-related macular degeneration; retinitis pigmentosa; glaucoma; ocular hypertension; optic nerve and pathway disorders, such as papilledema, papillitis, retrobulbar neuritis, toxic amblyopia, optic atrophy, bitemporal hemianopia, and homonymous hemianopia. In certain preferred embodiments, the subject anti-angiogenic compounds are used as part of a treatment for uveitis, Diabetic Macular Edema (DME), Wet ARMD, and CMV retinitis.

There are various sustained release drug delivery devices for implantation in the eye and treating various eye diseases that can be readily adapted for delivery of the subject anti-angiogenic compounds. Examples are found in the following patents, the disclosures of which are incorporated herein by reference: U.S. 2005/0137583 (Renner); U.S. 2004/0219181 (Viscasillas); U.S. 2004/0265356 (Mosack); U.S. 2005/0031669 (Shafiee); U.S. 2005/0137538 (Kunzler); U.S. 2002/0086051A1 (Viscasillas); U.S. 2002/0106395A1 (Brubaker); U.S. 2002/0110591A1 (Brubaker et al.); U.S. 2002/0110592A1 (Brubaker et al.); U.S: 2002/0110635A1 (Brubaker et al.); U.S. Pat. No. 5,378,475 (Smith et al.); U.S. Pat. No. 5,773,019 (Ashton et al.); U.S. Pat. No. 5,902,598 (Chen et al.); U.S. Pat. No. 6,001,386 (Ashton et al.); U.S. Pat. No. 6,726,918 (Wong); U.S. Pat. No. 6,331,313 (Wong); U.S. Pat. No. 5,824,072 (Wong); U.S. Pat. No. 5,632,984 (Wong); U.S. Pat. No. 6,217,895 (Guo et al.); U.S. Pat. No. 6,375,972 (Guo et al.). In certain embodiments, the device include an inner drug core including the anti-angiogenic compound, and some type of holder for the drug core made of an impermeable material such as silicone or other hydrophobic materials. The holder includes one or more openings for passage of the pharmaceutically agent through the impermeable material to eye tissue. Many of these devices include at least one layer of material permeable to the active agent, such as polyvinyl alcohol.

BRIEF DESCRIPTION OF THE FIGURES

FIG. 1 is table of $IC_{50}$ values for Trifluridine, Mycophenolic acid, Danazol, Asparaginase, and Itraconazole.

FIG. 2 shows structure-activity relationships for imidazole and triazole compounds utilized in the invention.

FIG. 3 is a cell cycle analysis of bom endothelial cells and fibroblast cells for Fumagillin, Mycophenolic acid, Trifluridine, and Itraconazole.

FIG. 5 shows the inhibition of HUVEC by Mycophenolic acid and its reversal by guanine.

DETAILED DESCRIPTION OF THE INVENTION

I. Methods of Treatment

Figure 4:
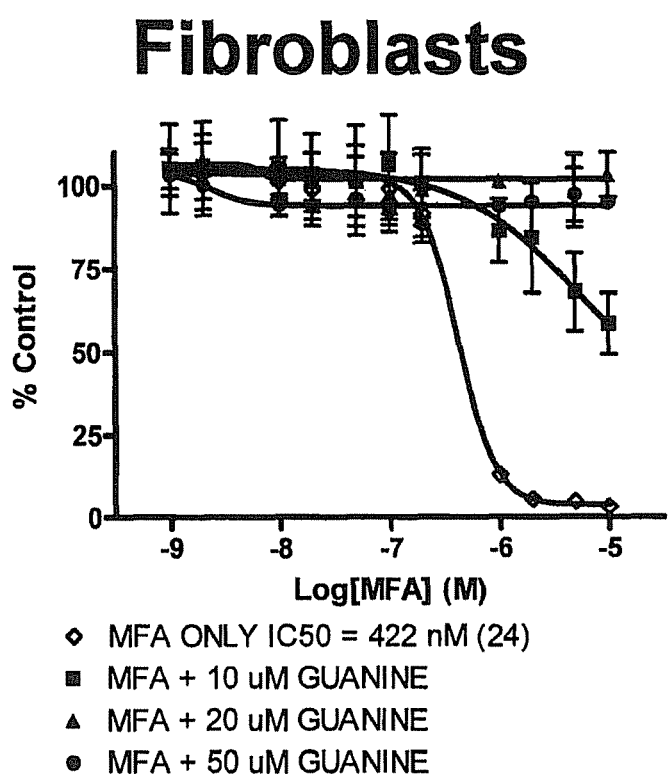
FIG. 4 shows the reversal of Mycophenolic acid inhibition by guanine.

The present invention is based on the discovery that various classes of compounds that have already been demonstrated as tolerable in human patients as part of other therapies, also have potent anti-angiogenic activities. In general, the compounds of the present invention inhibit endothelial cell proliferation. In certain preferred embodiments, the anti-angiogenic activity derives at least in part from the ability of the compound to inhibit progression through the G1/S point of the cell cycle.

In one aspect, the invention provides a method of inhibiting or otherwise reducing angiogenesis in a subject using a treatment protocol that includes administering a compound that inhibits inosine monophosphate dehydrogenase (IMPDH). As described in further detail below, it has been discovered that inhibition of IMPDH in endothelial cells can prevent their proliferation, and makes IMPDH inhibitors useful as anti-angiogenic agents. IMPDH is an enzyme in the de novo synthesis pathway of guanosine nucleotides. IMPDH catalyzes the NAD-dependent oxidation of inosine-5'-monophosphate (IMP) to xanthosine-5'-monophosphate (XMP). Two isoforms of human IMPDH have been identified. Type I is constitutive; Type II is inducible and is important in B- and T-lymphocytes.

The IMPDH inhibitors useful in the practice of the invention preferably have high potency for inhibition of IMPDH enzyme activity. In preferred embodiments, the EMPDH inhibitors have a Ki less than about 1 micromolar, and more preferably have Ki less than about 100 nM. In the most preferred embodiments, the IMPDH inhibitors have Ki less than about 50 nM. While not wishing to be bound by any particular theory, in embodiments wherein the subject IMPDH inhibitors are used systemically, or otherwise where they are being delivered to tissue in which both isoforms are expressed, the use of inhibitors that are selective for the type I isoform may be preferred. In those embodiments, exemplary IMPDH inhibitors that can be used have a Ki that is at least 2 fold greater (i.e., is less potent an inhibitor) for the type II isoform relative to the type I isoform, and more preferably at least 5 fold, 10 fold, 50 fold or even 100 fold greater. Where bioavailability of the inhibitor may influence the relative potency, exemplary IMPDH inhibitors that can be used have an EC50 that is at least 2 fold greater (i.e., is less potent an inhibitor) for the type II isoform relative to the type I isoform, and more preferably at least 5 fold, 10 fold, 50 fold or even 100 fold greater.

In certain embodiments, the use of an IMPDH inhibitor in treatment involves dosing the patient to produce a serum or local concentration, as appropriate, that is at least 50 percent less than the EC50 for inhibiting MPDH in lymphocytes, e.g., such that the dose is sub-immunosuppressive, and even more preferably at least 1 or even 2 orders of magnitude less than the EC50 for inhibiting IMPDH in lymphocytes.

In an exemplary embodiment, the subject IMPDH inhibitor is a mycophenolate. As used herein, "mycophenolates" refers herein to mycophenolic acid and its analogs, and their pharmaceutically acceptable salts, derivatives, prodrugs, and metabolites. Exemplary mycophenolates for use in the present invention include mycophenolic acid and mycophenylate mofetil. Mycophenolic acid, or 6-(4-hydroxy-6-methoxy-7-methyl-3-oxo-1,3-dihydroisobenzofuran-5-yl)-4-methyl-hex-4-enoic acid, has the structure

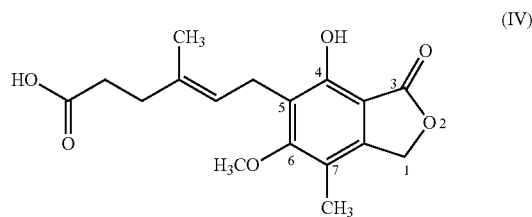 [SMILES: COc1c(C)c2c(c(O)c1C/C=C(\C)CCC(=O)O)C(=O)OC2]

(IV)

Mycophenolate mofetil is the 2-morpholinoethyl ester of mycophenolic acid, and has the formula:

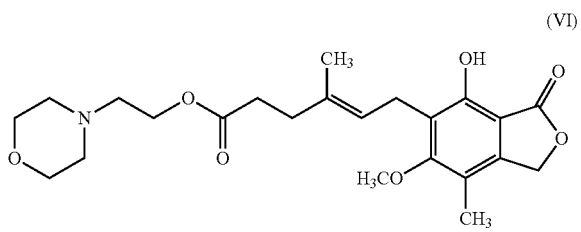 [SMILES: COc1c(C)c2c(c(O)c1C/C=C(\C)CCC(=O)OCCN1CCOCC1)C(=O)OC2]

(VI)

Analogs of mycophenolic acid that have high IMPDH-inhibiting activity are also useful in the practice of the present invention include compounds with varying substituents in the 2-, 4-, 5-, and 6-positions on the mycophenolate core structure, as well as pharmaceutically acceptable salts, derivatives, prodrugs, and metabolites of such mycophenolate analogs. Such compounds are described extensively in the U.S. patents tabulated below and incorporated herein by reference.

U.S. Pat. No. 5,688,529 Mycophenolate mofetil high dose oral suspensions

U.S. Pat. No. 5,633,279 5-Substituted derivatives of mycophenolic acid

U.S. Pat. No. 5,554,612 4-Amino-6-substituted mycophenolic acid and derivatives

U.S. Pat. No. 5,538,969 4-Amino derivatives of 5-substituted mycophenolic acid

U.S. Pat. No. 5,536,747 6-Substituted mycophenolic acid and derivatives

U.S. Pat. No. 5,493,030 5-Substituted derivatives of mycophenolic acid

U.S. Pat. No. 5,444,072 6-Substituted mycophenolic acid and derivatives

U.S. Pat. No. 5,441,953 4-Amino derivatives of mycophenolic acid

U.S. Pat. No. 5,380,879 Derivatives of mycophenolic acid

U.S. Pat. No. 4,861,776 Heterocyclic aminoalkyl esters of mycophenolic acid and derivatives thereof U.S. Pat. No. 4,753,935 Morpholinoethylesters of mycophenolic acid U.S. Pat. No. 4,748,173 Heterocyclic aminoalkyl esters of mycophenolic acid and derivatives thereof U.S. Pat. No. 4,727,069 Heterocyclic aminoalkyl esters of mycophenolic acid, derivatives thereof Other IMPDH inhibitors that may be useful in the present invention include Ribavarin; BMS-337197; VX-497 (merimepodib); VX-148; VX-944; Viramidine; Levovirin; Mizoribine; Mizoribine aglycone; benzamide riboside, selenazofurin. See also U.S. Pat. No. 5,807,876, issued Sep. 15, 1998, "Inhibitors of IMPDH Enzyme". Other IMPDH inhibitors include Tiazofurin and related compounds. Tiazofurin is anabolized to become an NAD analog that inhibits IMPDH. Tiazofurin may be prepared as described in U.S. Pat. No. 4,680,285 or U.S. Pat. No. 4,451,648.

Still other IMPDH inhibitors useful according to the present invention include the nicotinamide adenine dinucleotide (NAD) analogs, such as disclosed in Pankiewicz et al. (1997) Pharmacol Ther. 76(1-3): 89-100 and Pankiewicz et al. (2002) J Med Chem. 45(3):703-12. These analogues contain 5-beta-D-ribofuranosylnicotinamide (C-NAD), 6-beta-D-ribofuranosylpicolinamide (C-PAD), 3-beta-D-ribofuranosylbenzamide (BAD), and 2-beta-D-ribofuranosylthiazole4-carboxamide (TAD) in place of the nicotinamide riboside moiety, and are reported to have potent inhibitory activity against the enzyme in the form of pyrophosphates, as well as metabolically stable methylene- and difluoromethylenebis(phosphonate)s. Fluorination at the C2' (ribo and arabino configuration) and C3' (ribo) of the adenosine moiety of TAD yields analogues highly potent against IMPDH. Further, NAD analogues containing difluoromethylene linkage are highly effective in inhibition of K562 cell growth, as well as potent inducers of K562 cell differentiation. In certain embodiments, the IMPDH inhibitor is 5-ethynyl-1-β-D-ribofuranosylimidazole-4-carboxamide (EICAR) or the methylenebis(phosphonate) analogs C2-MAD and C4-MAD, which can be obtained by coupling 2',3'-O-isopropylideneadenosine 5'-methylenebis(phosphonate) with mycophenolic alcohols.

In one aspect, the invention provides a method of inhibiting angiogenesis in a subject, the method comprising the step of administering to the subject an angiogenesis-inhibiting compound, wherein the compound is selected from the following: Mycophenolic Acid; Ribavarin; Mycophenolate;

Mycophenylate Mofetil; BMS-337197; VX-497 (merimepodib); VX-148; VX-944; Viramidine; Levovirin; Mizoribine; Tiazofurin; benzamide riboside, selenazofurin, 5-ethynyl-1-β-D-ribofuranosylimidazole-4-carboxamide (EICAR); and C2-MAD.

In another aspect, the invention provides a method of inhibiting angiogenesis in a subject, the method comprising the step of administering to the subject an angiogenesis-inhibiting compound, wherein the compound is selected from the following: Mycophenolic Acid; Ribavarin; Mycophenolate; Mycophenylate Mofetil; BMS-337197; VX-497 (merimepodib); VX-148; VX-944; Viramidine; Levovirin; Mizoribine; Tiazofurin; benzamide riboside, selenazofurin, 5-ethynyl-1-β-D-ribofuranosylimidazole-4-carboxamide (EICAR); and C2-MAD; wherein the compound inhibits inosine monophosphate dehydrogenase (IMPDH).

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is selected from the following: Mycophenolic Acid; Ribavarin; Mycophenolate; Mycophenylate Mofetil; BMS-337197; VX-497 (merimepodib); VX-148; VX-944; Viramidine; Levovirin; Mizoribine; Tiazofurin; benzamide riboside, selenazofurin, 5-ethynyl-1-β-D-ribofuranosylimidazole-4-carboxamide (EICAR); and C2-MAD.

In a certain embodiment, the compound is capable of inhibiting inosine monophosphate dehydrogenase (IMPDH).

In still another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is selected from the following: Mycophenolic Acid; Ribavarin; Mycophenolate; Mycophenylate Mofetil; BMS-337197; VX-497 (merimepodib); VX-148; VX-944; Viramidine; Levovirin; Mizoribine; Tiazofurin; benzamide riboside, selenazofurin, 5-ethynyl-1-β-D-ribofuranosylimidazole-4-carboxamide (EICAR); and C2-MAD; wherein the compound inhibits inosine monophosphate dehydrogenase (IMPDH).

In another aspect, the invention provides a method of treating a subject identified as suffering from or susceptible to a disease or disorder associated with angiogenesis, the method comprising the step of administering to the subject a therapeutic amount of an angiogenesis-inhibiting compound sufficient to treat the disease or disorder or symptoms thereof associated with angiogenesis under conditions such that the disease or disorder associated with angiogenesis is treated, wherein the compound is selected from the following: Mycophenolic Acid; Ribavarin; Mycophenolate; Mycophenylate Mofetil; BMS-337197; VX-497 (merimepodib); VX-148; VX-944; Viramidine; Levovirin; Mizoribine; Tiazofurin; benzamide riboside, selenazofurin, 5-ethynyl-1-β-D-ribof-uranosylimidazole-4-carboxamide (EICAR); and C2-MAD; wherein the compound inhibits inosine monophosphate dehydrogenase (IMPDH).

In still another aspect, the invention provides a method of inhibiting angiogenesis in a subject, comprising modulating IMPDH isoform I by administration of a compound selected from the following: Mycophenolic Acid; Ribavarin; Mycophenolate; Mycophenylate Mofetil; BMS-337197; VX-497 (merimepodib); VX-148; VX-944; Viramidine; Levovirin; Mizoribine; Tiazofurin; benzamide riboside, selenazofurin, 5-ethynyl-1-β-D-ribof-uranosylimidazole 4 carboxamide (EICAR); and C2-MAD; to a subject identified as in need of such treatment.

In another aspect, the invention provides a method of inhibiting angiogenesis in a subject, treating a subject identified as suffering from or susceptible to a disease or disorder associated with angiogenesis, or any method delineated herein, wherein the subject is identified as to be in need of such treatment (e.g., angiogenesis reduction or inhibition).

In a certain embodiment, the IMPDH is isoform I. In a certain embodiment, the angiogenesis-inhibiting compound is MPA:

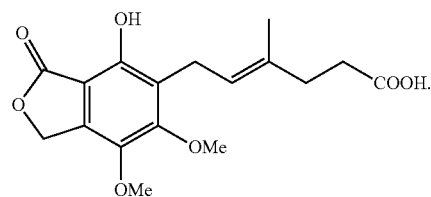 [SMILES: COc1c(C/C=C(\C)CCC(=O)O)c(O)c2c(c1OC)COC2=O]

In a certain embodiment, the angiogenesis-inhibiting compound inhibits endothelial cell proliferation. In a certain embodiment the angiogenesis-inhibiting compound is a GI/S cell cycle inhibitor. In a certain embodiment, the angiogenesis-inhibiting compound decreases new blood vessel formation.

In another aspect, the invention provides a method of inhibiting angiogenesis in a subject, the method comprising the step of administering to the subject an angiogenesis-inhibiting compound, wherein the compound is selected from the following: Miconazole, Amphotericin B, Clotrimazole, Econazole, Griseofulvin, Fluconazole, Ketoconazole, Miconazole, Nystatin, Itraconazole, Voriconazole, Clotrimazole, Caspofungin, Allylamines, Thiocarbamates, 5-fluorocytosine, Flucytosine, Epoxytriazole derivatives, Terbinafine, Echinocandins, Tioconazole, Terconazole, Butoconazole Nitrate, Unecylenic Acid, Clioquinol, Ciclopirox Olamine, Econazole Nitrate, Triacetin, and Tolnaftate.

In still another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is selected from the following: Miconazole, Amphotericin B, Clotrimazole, Econazole, Griseofulvin, Fluconazole, Ketoconazole, Miconazole, Nystatin, Itraconazole, Voriconazole, Clotrimazole, Caspofungin, Alrylamines, Thiocarbamates, 5-fluorocytosine, Flucytosine, Epoxytriazole derivatives, Terbinafrae, Echinocandins, Tioconazole, Terconazole, Butoconazole Nitrate, Unecylenic Acid, Clioquinol, Ciclopirox Olamine, Econazole Nitrate, Triacetin, and Tolnaftate.

In yet another aspect, the invention provides a method of treating a subject identified as suffering or susceptible to a disease or disorder associated with angiogenesis, the method comprising fee step of administering to the subject a therapeutic amount of an angiogenesis-inhibiting compound sufficient to treat the disease or disorder or symptoms thereof associated with angiogenesis under conditions such that the disease or disorder associated with angiogenesis is treated, wherein the compound is selected from the following: Miconazole, Amphotericin B, Clotrimazole, Econazole, Griseofulvin, Fluconazole, Ketoconazole, Miconazole, Nystatin, Itraconazole, Voriconazole, Clotrimazole, Caspofungin, Allylamines, Thiocarbamates, 5-fluorocytosine, Flucytosine, Epoxytriazole derivatives, Terbinaftae, Echinocandins, Tioconazole, Terconazole, Butoconazole Nitrate, Unecylenic Acid, Clioquinol, Ciclopirox Olamine, Econazole Nitrate, Triacetin, and Tolnaftate.

In another aspect, the invention provides a method of inhibiting angiogenesis in a subject, the method comprising the step of administering to the subject an angiogenesis-inhibiting compound, wherein the compound is selected from the following: trifluridine, danazol, and asparaginase.

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is selected from the following: trifluridine, danazol, and asparaginase.

In still another aspect, the invention provides a method of treating a subject identified as suffering from or susceptible to a disease or disorder associated with angiogenesis, the method comprising the step of administering to the subject a therapeutic amount of an angiogenesis-inhibiting compound sufficient to treat the disease or disorder or symptoms thereof associated with angiogenesis under conditions such that the disease or disorder associated with angiogenesis is treated, wherein the compound is selected from the following: trifluridine, danazol, and asparaginase.

In another aspect, the invention provides a method of inhibiting angiogenesis in a subject, the method comprising the step of administering to the subject an angiogenesis-inhibiting compound, wherein the compound is an imidazole compound of formula I:

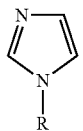

I wherein R is selected from:

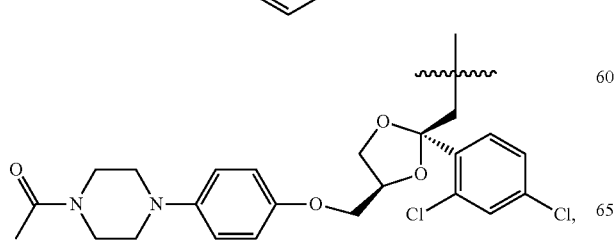

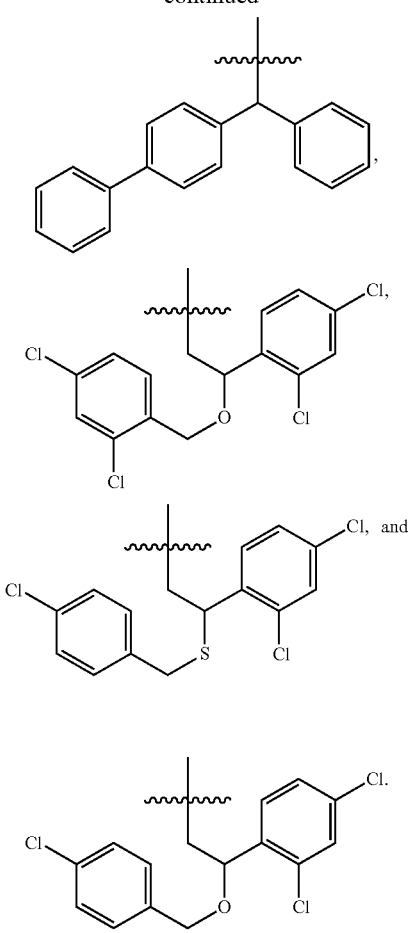

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is an imidazole compound of formula I:

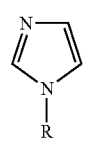

I wherein R is selected from:

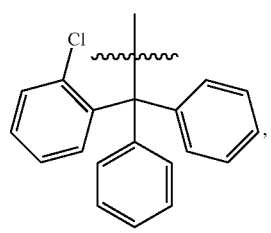

-continued

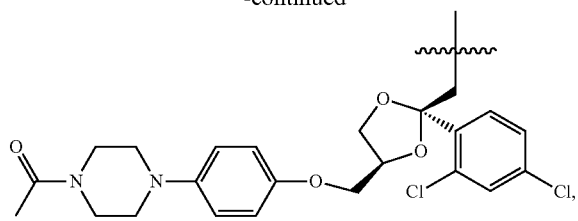

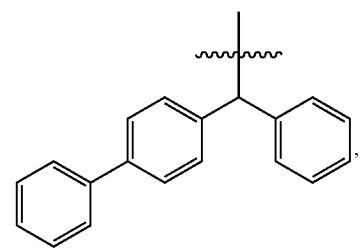

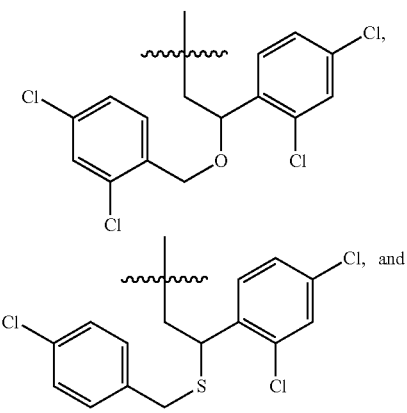

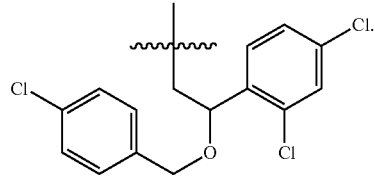

In still another aspect, the invention provides a method of treating a subject identified as suffering from or susceptible to a disease or disorder associated with angiogenesis, the method comprising the step of administering to the subject a therapeutic amount of an angiogenesis-inhibiting compound sufficient to treat the disease or disorder or symptoms thereof associated with angiogenesis under conditions such that the disease or disorder associated with angiogenesis is treated, wherein the compound is an imidazole compound of formula I:

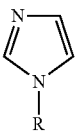

I wherein R is selected from:

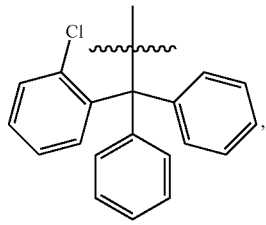

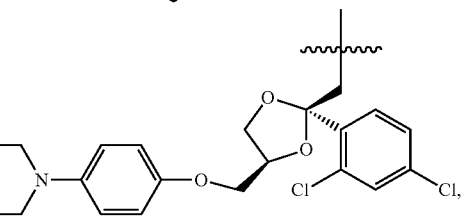

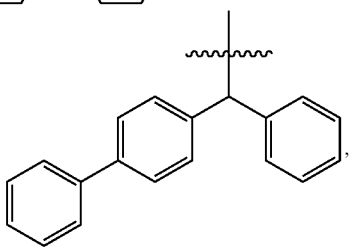

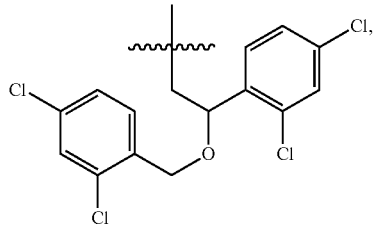

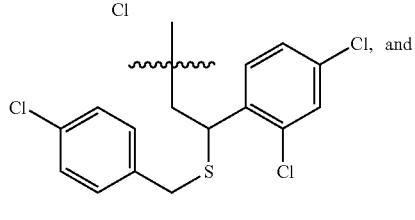

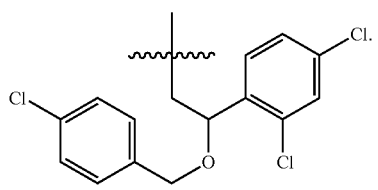

In a certain embodiment, the imidazole compound is Clotrimazole:

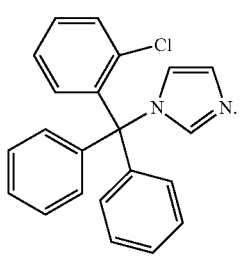 [SMILES: Clc1ccccc1C(c1ccccc1)(c1ccccc1)n1ccnc1]

In a certain embodiment, the imidazole compound is Ketoconazole:

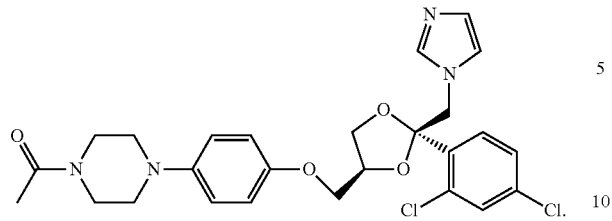

In a certain embodiment, the imidazole compound is Bifonazole:

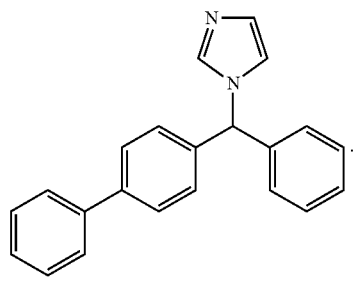 [SMILES: c1ccc(-c2ccc(C(c3ccccc3)n3ccnc3)cc2)cc1]

In a certain embodiment, the imidazole compound is Miconazole:

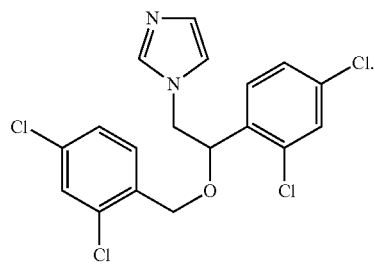 [SMILES: Clc1ccc(COC(Cn2ccnc2)c2ccc(Cl)cc2Cl)c(Cl)c1]

In a certain embodiment, the imidazole compound is Sulconazole:

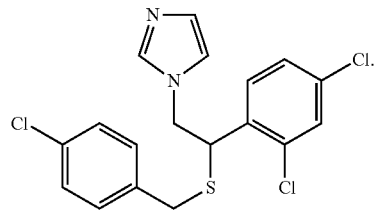 [SMILES: Clc1ccc(CSC(Cn2ccnc2)c2ccc(Cl)cc2Cl)cc1]

In a certain embodiment, the imidazole compound is Econazole:

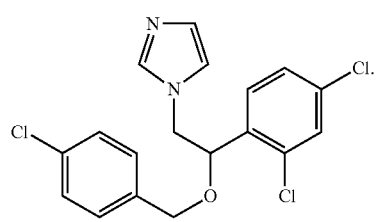 [SMILES: Clc1ccc(COC(Cn2ccnc2)c2ccc(Cl)cc2Cl)cc1]

In another aspect, the invention provides a method of inhibiting angiogenesis in a subject, the method comprising the step of administering to the subject an angiogenesis-inhibiting compound, wherein the compound is a triazole compound of formula II:

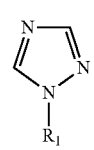

II wherein, $R_1$ is

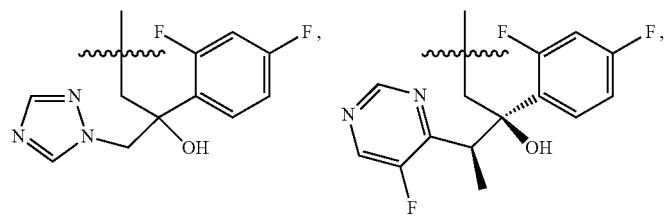

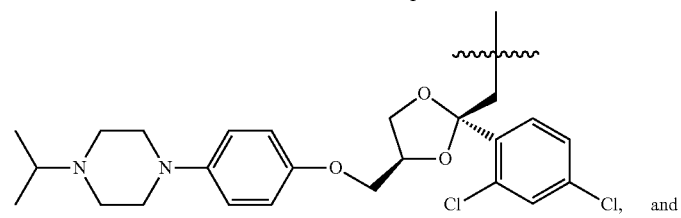

and

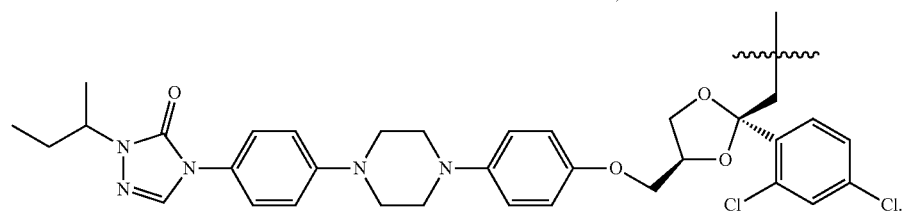

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is a triazole compound of formula II:

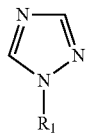
II wherein, $R_1$ is

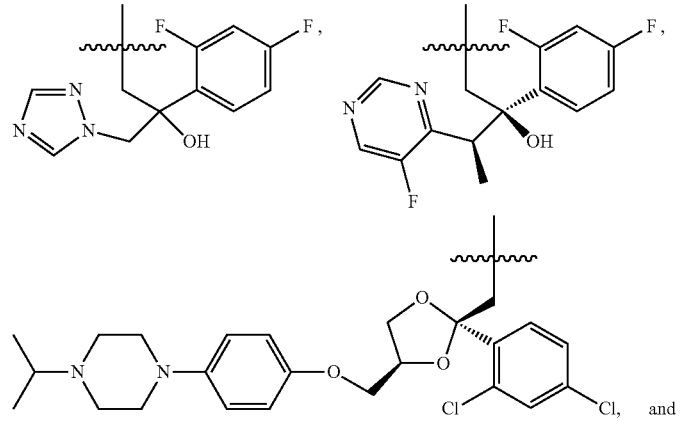

In still another aspect, the invention provides a method of treating a subject identified as suffering from or susceptible to a disease or disorder associated with angiogenesis, the method comprising the step of administering to the subject a therapeutic amount of an angiogenesis-inhibiting compound sufficient to treat the disease or disorder or symptoms thereof associated with angiogenesis under conditions such that the disease or disorder associated with angiogenesis is treated, wherein the compound is a triazole compound of formula

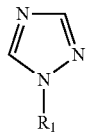
II wherein $R_1$ is

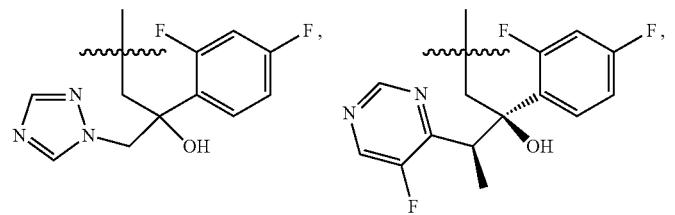

-continued

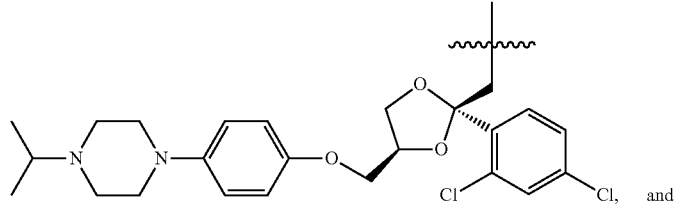

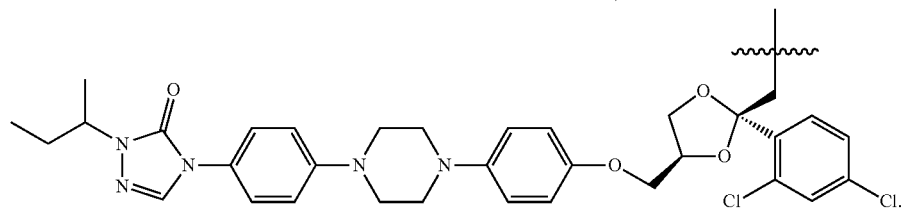

In a certain embodiment, the triazole compound is Fluconazole:

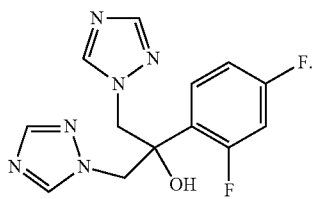 [SMILES: OC(Cn1cncn1)(Cn1cncn1)c1ccc(F)cc1F]

In a certain embodiment the triazole compound is Voriconazole:

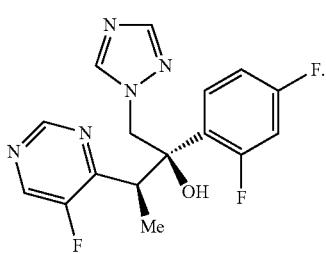 [SMILES: C[C@@H](c1ncncc1F)[C@](O)(Cn1cncn1)c1ccc(F)cc1F]

In a certain embodiment the triazole compound is Itraconazole:

In a certain embodiment the triazole compound is Terconazole:

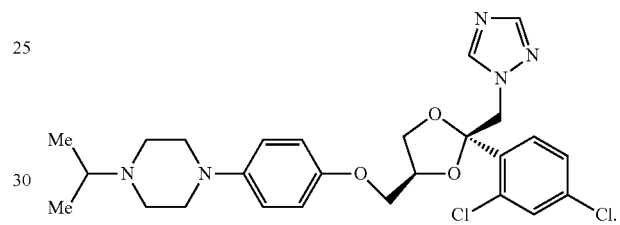

In a certain embodiment, itraconazole inhibits angiogenesis by inhibiting endothelial cell proliferation. In another embodiment, itraconazole is a GI/S cell cycle inhibitor.

In a certain embodiment, the invention further comprises an additional therapeutic agent. In a further embodiment, the additional therapeutic agent is an angiogenesis-inhibiting compound. In another further embodiment, the additional therapeutic agent is an anticancer compound.

In a certain embodiment, the disease or disorder associated with angiogenesis is selected from: tumor or cancer growth (neoplasia), skin disorders, neovascularization, and inflammatory and arthritic diseases.

In a certain embodiment, the step of administering the angiogenesis-inhibiting compound comprises administering the compound orally, topically, parentally, intravenously or intramuscularly.

In a certain embodiment, the step of administering the angiogenesis-inhibiting compound comprises administering the compound in a dosage of between about 0.1 and 100 mg/kg/day. In another embodiment, the step of administer-

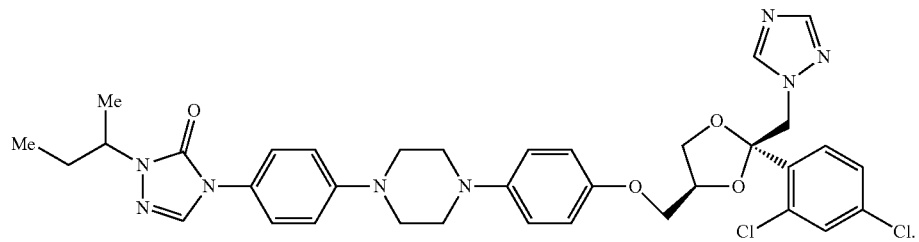 [SMILES: CCC(C)n1ncn(-c2ccc(N3CCN(c4ccc(OC[C@H]5CO[C@](Cn6cncn6)(c6ccc(Cl)cc6Cl)O5)cc4)CC3)cc2)c1=O]

ing the angiogenesis-inhibiting compound comprises administering the compound in a dosage of less than about 500 mg/day.

In a certain embodiment, the subject is a human.

In a certain embodiment, the invention provides a kit comprising an effective amount of an angiogenesis-inhibiting compound in unit dosage form, together with instructions for administering the angiogenesis-inhibiting compound to a subject suffering from or susceptible to a disease or disorder or symptoms thereof associated with angiogenesis. In a further embodiment, the angiogenesis-inhibiting compound is MPA.

In a certain embodiment, the invention provides administering an effective amount of a composition comprising an angiogenesis-inhibiting compound and a pharmaceutically suitable excipient.

A screening of a clinical drug library in an endothelial cell proliferation assay was carried out, and several hits were identified with $IC_{50}$ values below 1 μM. Herein is reported the characterization of one of the most potent hits, the known immunosuppressive drug mycophenolic acid (MPA). It is demonstrated here that MPA inhibits endothelial cells by the same mechanism as it does T and B lymphocytes. Like T and B cells, treatment of endothelial cells with MPA leads to cell cycle arrest in the G1 phase, which can be reversed by addition of guanine or guanosine, suggesting that inosine monophosphate dehydrogenase is the target. Of the two isoforms of IMPDH expressed in humans, siRNA knockdown of IMPDH-1 is sufficient to cause G1 cell cycle arrest while knockdown of IMPDH-2 led to a delay in the progression within the S phase. MPA effectively blocks new blood vessel formation in response to bFGF and VEGF in a matrigel plug assay and inhibits angiogenesis in a mouse renal cell carcinoma model in vivo.

The selectivity of MPA for T and B lymphocytes was thought to be due to dependence on the de novo nucleotide synthesis pathway for proliferation. Endothelial cells, along with smooth muscle cells, fibroblasts, and epithelial cells, were thought to be less sensitive to blockade of de novo nucleotide synthesis as inhibition of proliferation is seen at relatively high concentrations of MPA compared to T and B cells (Mohacsi, P. J., Tuller, D., Hulliger, B. & Wijngaard, P. L. (1997) *J. Heart. Lung. Transplant.* 16, 484-492, Eugui, E. M., Almquist, S. J., Muller, C. D. & Allison, A. C. (1991) *Scand. J. Immunol.* 33, 161-173). The reduced sensitivity of these cell types to MPA was attributed to use of the nucleotide salvage pathway. It is demonstrated here the unequivocal role of de novo nucleotide synthesis in regulating endothelial cell proliferation. MPA is as potent at inhibiting the proliferation of HUVEC as Jurkat T-cells (FIG. 5B vs. 5C) as well as primary T and B cells as reported previously (Eugui, E. M., Almquist, S. J., Muller, C. D. & Allison, A. C. (1991) *Scand. J. Immunol.* 33, 161-173). Unlike T cells, however, it was found that much higher concentrations of guanosine are required to completely reverse inhibition in HUVEC (FIG. 5B), indicating de novo nucleotide synthesis plays a more essential role in endothelial cell proliferation than in T and B cells. This difference in dependence on de novo nucleotide synthesis between endothelial and T cells raised the possibility that angiogenesis may be more susceptible to inhibition by MPA in vivo.

MPA and its prodrug form, mycophenolate mofetil, have been in clinical use for a number of years as an immunosuppressant. Its peak plasma level in human renal transplant patients undergoing chronic oral treatment is 75 μM with a half life of 18 hours, which is nearly 750-fold higher than the $IC_{50}$ values for inhibition in endothelial cells (Roche Laboratories, I. (2003), 1-34). MPA has been shown to inhibit the growth of tumor cells in vitro and in mouse xenografts (Carter, S. B., Franklin, T. J., Jones, D. F., Leonard, B. J., Mills, S. D., Turner, R. W. & Turner, W. B. (1969) *Nature* 223, 848-850). This observation lead to testing of MPA in small cohorts of patients (<35) with a variety of cancers in the 1970s (Knudtzon, S. & Nissen, N. I. (1972) *Cancer Chemother. Rep.* 56, 221-227, Brewin, T. B., Cole, M. P., Jones, C. T., Piatt, D. S. & Todd, I. D. (1972) *Cancer Chemother, Rep.* 56, 83-87). As the diethanolamine salt of MPA was used rather than the currently prescribed mofetil prodrug, considerable dose-limiting gastrointestinal toxicity occurred (Knudtzon, S. & Nissen, N. I. (1972) *Cancer Chemother. Rep.* 56, 221-227). Using the mouse Matrigel angiogenesis assay and the RENCA tumor model, it was demonstrated that MPA blocks VEGF and bFGF stimulated angiogenesis and tumor associated angiogenesis. This suggests that in addition to a direct anti-proliferative effect on cancer cells, MPA can block tumor growth by inhibiting new blood vessel formation. Given the current understanding of angiogenesis, MPA would be expected to slow the rate of tumor progression-, which was not the endpoint used in previous studies in cancer patients (Knudtzon; S. & Nissen, N. I. (1972) *Cancer Chemother, Rep.* 56, 221-227, Brewin, T. B., Cole, M. P., Jones, C. T., Piatt, D. S. & Todd, I. D. (1972) *Cancer Chemother. Rep.* 56, 83-87). Furthermore, our demonstration of the in vivo anti-angiogenic effect of MPA suggests this drug could potentially be used to treat other diseases characterized by inappropriate new blood vessel formation.

Although the inhibitory effects of MPA on endothelial cells have been observed previously, it was not clear whether the same molecular mechanism underlies the anti-angiogenic and the immunosuppressive effects. It is established for the first time that the anti-angiogenic activity of MPA in endothelial cells share the same molecular basis as its immunosuppressive effects in T and B cells by multiple criteria including G1/S cell cycle arrest and reversion of inhibition by guanine or guanosine. More importantly, MPDH is validated as the target for MPA in endothelial cells using RNA interference delivered through the non-invasive lentivirus transduction of primary endothelial cells. With isoform-specific siRNA constructs, it was found that knockdown of IMPDH-1 is sufficient to cause the same cell cycle effect in endothelial cells as MPA treatment. The physiological functions of both isoforms of IMPDH have been investigated using a gene knockout approach in mice. Of the two isoforms, IMPDH-2 appears to be more essential, as the homozygous knockout of murine IMPDH-2 led to early embryonic lethality (Gu, J. J., Stegmann, S., Gathy, K., Murray, R-, Laliberte, J., Ayscue, L. & Mitchell, B. S. (2000) *J. Clin. Invest.* 106, 599-606). In contrast, the IMPDH-1 null animal developed normally and exhibited no obvious defects (Gu, J. J., Tolin, A. K., Jain, J., Huang, H., Santiago, L. & Mitchell, B. S. (2003) *Mol. Cell. Biol.* 23, 6702-6712). Importantly, the function of T cells from proliferation to cytokine production was largely intact in IMPDH-1 knockout mice, suggesting that this isoform is dispensable for T cell development and function. Together, these findings raise the exciting possibility that isoform-specific inhibitors of IMPDH-1 may be selective for endothelial cells without affecting the immune system and devoid of the side effects of MPA and other existing nonselective IMPDH inhibitors.

In addition to MPA, a large number of new structural classes of IMPDH inhibitors have been identified or developed including the well-known antiviral drug ribavirin (Lee, H. J., Pawlak, K., Nguyen, B. T., Robins, R. K. & Sadee, W.

(1985) *Cancer Res.* 45, 5512-5520, Sintchak, M. D. & Nimmesgern, E. (2000) *Immunopharmacology* 47, 163-184).

This instant invention is based on the premise that there exist unappreciated physiological activities among known clinical drugs. This premise was proven by the identification of multiple known drugs with unexpected inhibitory effects on endothelial cell proliferation in vitro and angiogenesis in vivo. In addition to the endothelial cell proliferation assay, a library in a number of other cellular assays was screened. It was found that the hit rates with this drug library are significantly higher than commercially available small molecule libraries on more than half a dozen cellular screens. The molecular basis of these high hit rates may lie in the shared genome and largely overlapping proteome of all human cell types and tissues. Significant redundancy exists in the usage of individual genes in different physiological as well as pathological processes. Thus, there is great potential in screening existing drugs for novel biological and therapeutic activities.

II. Treatment of Diseases

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

As used herein, the terms "prevent," "preventing," "prevention," and the like refer to reducing the probability of developing a disorder or condition in a subject, who does not have, but is at risk of or susceptible to developing a disorder or condition.

The term "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "anti-angiogenic compound" and "angiogenesis inhibiting compound" may be used interchangeably.

The term "tumor" is used to describe an abnormal growth in tissue which occurs when cellular proliferation is more rapid than normal tissue and continues to grow after the stimuli that initiated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized.

The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor. Methods of treating tumors and/or cancer according to the present invention comprise administering to a patient in need thereof an effective amount of one or compounds according to the present invention.

Angiogenesis is used throughout the specification to describe me biological processes which result in the development of blood vessels or increase in the vascularity of tissue in an organism. Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases or disorders treated, ameliorated or prevented by the instant invention include the following: neoplasia, internal malignancies such as eye or ocular cancer, rectal cancer, colon cancer, cervical cancer, prostate cancer, breast cancer and bladder cancer, benign and malignant rumors, including various cancers such as, anal and oral cancers, stomach, rectal, liver, pancreatic, lung, cervix uteri, corpus uteri, ovary, prostate, testis, renal, mouth/pharynx, esophageal, larynx, kidney, brain/ens (e.g., gliomas), head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, lymphoma, neurofibromatosis, tuberous sclerosis (each of which conditions produces benign tumors of the skin), hemangiomas, lymphangiogenesis, rhabdomyosarcomas, retinoblastoma, osteosarcoma, acoustic neuroma, neurofibroma, trachoma, pyogenic granulomas, blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen, psoriasis, acne, rosacea, warts, eczema, neurofibromatosis, Sturge-Weber syndrome, venous ulcers of the skin, tuberous sclerosis, chronic inflammatory disease, arthritis, lupus, scleroderma, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium, keratitis sicca, Sjogren's, phylectenulosis, syphilis, Mycobacteria infections, lipid degeneration, chemical burns, bacterial ulcers, fungal ulcers, herpes simplex infections, herpes zoster infections, protozoan infections, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, diabetic retinopathy, macular edema, macular degeneration, sickle cell anemia, sarcoid, pseudoxanthoma elasticum, Pagefs disease, vein occlusion, artery occlusion, carotid obstructive disease, chronic uveitis/vitritis, Lyme disease, systemic lupus erythematosus, Bales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, rubeosis (neovascularization of the ankle), diseases caused by the abnormal proliferation of fibrovascular or fibrous tissue including all forms of proliferative vitreoretinopathy, whether or not associated with diabetes, neovascular disease, pannus, diabetic macular edema, vascular retinopathy, retinal degeneration, inflammatory diseases of the retina, proliferative vitreoretinopathy, diseases associated with rubeosis (neovascularization of the ankle), diseases caused by the abnormal proliferation of fibrovascular or fibrous tissue including all forms of proliferative vitreoretinopathy, Crohn's disease and ulcerative colitis, sarcoidosis, osteoarthritis, inflammatory bowel diseases, skin lesions, Osler-Weber-Rendu disease, or hereditary hemorrhagic telangiectasia, osteoarthritis, Sarcoidosis, skin lesions, acquired immune deficiency syndrome, and small bowel obstruction.

The inhibition of angiogenesis in treating or reversing the disease state or condition is an important aspect of the present invention. More particularly, the present invention relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Treatment of internal malignancies such as eye or ocular cancer, rectal cancer, colon cancer, cervical cancer, prostate cancer, breast cancer and bladder cancer, among numerous others, and oral malignancies are also contemplated by the present invention.

Angiogenesis inhibiting compounds of the present invention are used to treat, ameliorate or prevent benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/ens (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Angiogenesis is prominent in solid tumor formation and metastasis.

Angiogeneic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow mat give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention or control of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means can lead to cessation of the recurrence of the tumors.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenic disease, angiogenic disorder and angiogenic skin disorder are used throughout the specification to describe a disorder, generally a skin disorder or related disorder which occurs as a consequence of or which results in increased vascularization in tissue. Any skin disorder which has as a primary or secondary characterization, increased vascularization, is considered an angiogenic skin disorder for purposes of the present invention and is amenable to treatment with compounds according to the present invention.

Methods for treating, ameliorating, or preventing angiogenic skin disorders such as psoriasis, acne, rosacea, warts, eczema, hemangiomas, lymphangiogenesis, neurofibromatosis, Sturge-Weber syndrome, venous ulcers of the skin, tuberous sclerosis, chronic inflammatory disease and arthritis, as well as inflammation such as chronic inflammatory disease, including arthritis, lupus and scleroderma are also contemplated by the present invention, such methods comprising administering a therapeutically effective amount of one or more of the disclosed compounds to a patient in need of such treatment.

Diseases associated with neovascularization include optic disc neovascularization, iris neovascularization, retinal neovascularization, choroidal neovascularization, corneal neovascularization, and intravitreal neovascularization.

Diseases associated with corneal neovascularization and retinal/choroidal neovascularization that can be treated, ameliorated, or prevented, according to the present invention include but are not limited to, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, macular edema, macular degeneration,' sickle cell anemia, sarcoid, syphilis, pseudoxanthoma elasticum, Paget's-disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best1 s disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle), diseases caused by the abnormal proliferation of fibro vascular or fibrous tissue including all forms of proliferative vitreoretinopathy, whether or not associated with diabetes, and corneal graft rejection.

In some embodiments, the corneal neovascularization to be treated or inhibited is caused by trauma, chemical burns or corneal transplantation. In other particular embodiments, the iris neovascularization to be treated or inhibited is caused by diabetic retinopathy, vein occlusion, ocular tumor or retinal detachment. In still other particular embodiments, the retinal or intravitreal neovascularization to be treated or inhibited is caused by diabetic retinopathy, vein occlusion, sickle cell retinopathy, retinopathy of prematurity, retinal detachment, ocular ischemia or trauma. Additional diseases associated with choroidal neovascularization to be treated or inhibited are caused by retinal or subretinal disorders of age-related macular degeneration, diabetic macular edema, presumed ocular histoplasmosis syndrome, myopic degeneration, angioid streaks or ocular trauma.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium.

Diseases associated with chronic inflammation and arthritis can be treated, ameliorated or prevented by the compositions and methods of the present invention. Diseases with symptoms of chronic inflammation include inflammatory bowel diseases such as Crohn's disease and ulcerative colitis, psoriasis, sarcoidosis, rheumatoid arthritis, osteoarthritis, lupus and scleroderma. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state.

The compositions and methods of the present invention can be used to treat, ameliorate or prevent disease in patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease is active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease (or symptoms thereof) which can be treated, ameliorated or prevented according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Another disease that can be treated according to the present invention are Osler-Weber-Rendu disease, or hereditary hemorrhagic telangiectasia, and acquired immune deficiency syndrome.

Factors associated with angiogenesis may also have a role in osteoarthritis. The activation of the chondrocytes by angiogeneic-related factors contributes to the destruction of the joint. At a later stage, the angiogeneic factors would promote new bone formation. Therapeutic intervention that prevents the bone destruction could halt the progress of the disease and provide relief for persons suffering with arthritis.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula, thereby preventing conception.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

The present compounds may be used to treat subjects including animals, and in particular, mammals, including humans, as patients. Thus, humans and other animals, and in particular, mammals, suffering from diseases or disorders related to angiogenesis, can be treated, ameliorated or prevented by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated). Treatment according to the present invention can also be administered in conjunction with other conventional therapies, e.g., cancer therapy, such as radiation treatment or surgery.

Examples of IMPDH inhibitors, utilized in the present invention as inhibitors of angiogenesis, and utilized to treat diseases or disorders associated with angiogenesis include, but are by no means limited to the following: Ribavarin; Mycophenolic Acid; Mycophenylate Mofetil; BMS-337197; VX-497 (merimepodib); Viramidine; Mizoribine; Tiazofurin; VX-148; VX-944; Levovirin; benzamide riboside, thiophenfurin; selenophenfurin; imidazofurin; selenazofurin, 5-ethynyl-1-.beta.-D-ribofuranosylimidazole-4-carboxamide (EICAR); C2-MAD; C4-MAD, C6-MAD, 6-chloropurine riboside monophosphates, 4-thio-D-ribofuranose derivatives, 4-{3-[(3-Methoxy-4-oxazol-5-yl-phenylaminooxalyl)-amino]-3-methyl-butoxyl}-benzoic acid, 3-Methoxy-4-oxazol-5-yl-phenylamine, 4-Methoxy-naphthalene-1-carbonitrile, 1-(5-Methoxy-1H-indol-3-yl)-2-(pyridin-4-ylsulfanyl)-ethanone, 1H-Indole-3-carbonitrile, 2-(3-Dimethylamino-indan-5-yl)-7-methoxy-6-oxazol-5-yl-1H-quinolin-4-one, 7-Methoxy-6-oxazol-5-yl-2-m-tolyl-1H-quinolin-4-one, (3-Methoxy-4-oxazol-5-yl-phenyl)-(5-phenyl-oxazol-2-yl)-amine, 1-Methyl-6-(5-phenyl-oxazol-2-ylamino)-1H-indole-3-carbonitrile derivatives, bicyclic pyrazol-4,6-dione derivatives, 6-Benzoyl-3-ethyl-3-p-tolyl-1,5-diaza-bicyclo[3.1.0]hexane-2,4-dione, 3,3-Diethyl-2,4-dioxo-1,5-diaza-bicyclo[3.1.0]hexane-6-carboxylic acid ethyl ester, 3-Ethyl-2,4-dioxo-3-phenyl-1,5-diaza-bicyclo[3.1.0]hexane-6-carboxylic acid ethyl ester, 3-Ethyl-2,4-di-oxo-3-p-tolyl-1,5-diaza-bicyclo[3.1.0]hexane-6-carboxylic acid ethyl ester, 1-1H-1,2,4-triazole-3-carboxamide-2-morpholin-4-ylethyl 6-(4-hydroxy-6-methoxy-7-methyl-3-oxo-1H-isobenzofuran-5-yl)-4-methyl-hex-4-enoate; 6-(4-hydroxy-6-methoxy-7-methyl-3-oxo-1H-isobenzofuran-5-yl)-4-methyl-hex-4-enoic acid; sodium 6-(4-hydroxy-6-methoxy-7-methyl-3-oxo-1H-isobenzofuran-5-yl)-4-methyl-hex-4-enoate; tetrahydrofuran-3-yl[3-[[3-methoxy-4-(1,3-oxazol-5-yl)phenyl]carbamoylamino]phenyl]methylaminomethanoate; 1-[3,4-dihydroxy-5-(hydroxymethyl)tetrahydrofuran-2-yl]-1H-1,2,4-triazole-3-carboximidamide hydrochloride; 1-[3,4-dihydroxy-5-(hydroxymethyl)tetrahydrofuran-2-yl]-5-hydroxy-1H-imidazole-4-carboxamide; 2-(2,3-dihydroxy-4-methyl-cyclopentyl)-1,3-thiazole-4-carboxamide; 2-[3,4-dihydroxy-5-(hydroxymethyl)tetrahydrofuran-2-yl]-1,3-thiazole-4-carboxamide; [[5-(6-amino-9H-purin-9-yl)-3,4-dihydroxy-tetrahydrofuran-2-yl]methoxy-hydroxy-phosphoryl]methyl-[2-(4-hydroxy-6-methoxy-7-methyl-3-oxo-1H-isobenzofuran-5-yl)ethoxy]phosphinic acid; N-[3-(4-Hydroxy-phenoxy)-1,1-dimethyl-propyl]-N'-(3-methoxy-4-oxazol-5-yl-phenyl)-oxalamide; N-[3-Methoxy-4-(5-oxazolyl)phenyl]-N'-[3-(4-methoxyphenoxy)-1,1-dimethylpropyl]oxalamide; N-[3-Methoxy-4-(5-oxazolyl)phenyl]-N'41,1-dimethyl-3-(4-nitrophenoxyl)propyl]oxalamide; N-[3-(2-Hydroxyphenoxy)-1,1-dimethylpropyl]-N'-[3-methoxy-4-(5-oxazolyl)phenyl]oxalamide; N-[3-(4-Amino-phenoxy)-1,1-dimethyl-propyl]-N'-(3-methoxy-4-oxazol-5-yl-phenyl)-oxalamide; N-[3-(-Acetylamino-phenoxy)-1,1-dimethyl-propyl]-N'-(3-methoxy-4-oxazol-5-yl-phenyl)-oxalamide; N-[3-Methoxy-4-(5-oxazolyl)phenyl]-N'-[1,1-dimethyl-3-(3-pyridyloxy)propyl]oxalamide; N-[3-(3-hydroxyphenoxy)-1,1-dimethylpropyl]-1,1'-[3-methoxy-4-(5-oxazolyl)phenyl]oxalamide; N-[3-Methoxy-4-(5-oxazolyl)phenyl]-N'-[3-(3-methoxyphenoxy)-1,1-dimethylpropyl]oxalamide; N-[3-Methoxy-4-(5-oxazolyl)phenyl]-N'-[1,1-dimethyl-3-(3-nitrophenoxyl)propyl]oxalamide; N-[3-(3-Aminophenoxy)-1,1-dimethylpropyl]-N'-[3-methoxy-4-(5-oxazolyl)phenyl]oxalamide; 4-[3-[[[3-Methoxy-4-(5-oxazolyeanilio]oxalyl]amino]-3-methylbutoxy]benzoic acid; 2-[3-[[[3-Methoxy-4-(5-oxazolyl)anilino]oxalyl]amino]-3-methylbut-oxy]benzoic acid; 3-[3-[[[3-Methoxy-4-(5-oxazolyl)anilino]oxalyl]amino]-3-methylbutoxy]benzoic acid; 2-[4-[3-[[[3-Methoxy-4-(5-oxazolyl)anilino]oxalyl]amino]-3-methylbutoxy]phenoxy]acetic acid; 2-[2-[3-[[[3-Methoxy-4-(5-oxazolyl)anilino]oxalyl]amino]-3-methylbutoxy]phenoxy]acetic acid; N-[3-Methoxy-4-(5-oxazolyl)phenyl]-N-(1,1-dimethyl-3-phenoxypropyl)oxalamide; N-[3-Methoxy-4-(5-oxazolyl)phenyl]-N'-[1,1-dimethyl-3-(1-oxido-3-pyridyloxy)propyl]oxalamide; N-[3-(3,4-Dihydroxyphenoxy)-1,1-dimethylpropyl]-N'-[3-methoxy-4-(5-oxazolyl)phenyl]oxalamide; N-[3-Methoxy-4-(5-oxazolyl)phenyl]-N'-[1,1-dimethyl-3-[4-(methylcarbamoyl)phenoxy]propyl]oxalamide; N-[3-Methoxy-4-(5-oxazolyl)phenyl]-N-[3-(3,4-dimethoxyphenoxy)-1,1-dimethylpropyl]oxalamide; N-[3-[4-[(2-Hydroxyethyl)carbamoyl]phenoxy]-1,1-dimethyl-propyl]-N-[3-methoxy-4-(5-oxazolyl)phenyl]oxalamide; N-[3-(3-Chlorophenoxy)-1,1-dimethylpropyl]-N'-[3-methoxy-4-(5-oxazolyl)phenyl]oxalamide; N-[3-Methoxy-4-(5-oxazolyl)phenyl]-N'-[1,1-dimethyl-3-(3-pyridyloxy)propyl]oxalamide; N-[3-Methoxy-4-(5-oxazolyl)phenyl]-N-[1,1-dimethyl-3-(2-pyridyloxy)propyl]oxalamide; 2-[3-[[[3-Methoxy-4-(5-oxazolyl)anilino]oxalyl]amino]-3-methylbutoxy]phenyl]acetic acid; 2-[3-[3-[[[3-Methoxy-4-(5-oxazolyl)anilino]oxalyl]amino]-3-methylbutoxy]phenyl]acetic acid; 4-[2-[[[3-Methoxy-4-(5-oxazolyl)anilino]oxalyl]amino]-2-methylpropoxy]benzoic acid; 4-[3-[[[3-Methoxy-4-(5- oxazolyl)anilino]oxalyl]amino]-3-methylbutoxy]-2-methylbenzoic acid; 3-[3-[3-[[[3-Methoxy-4-(5-oxazolyl)anilino]oxalyl]amino]-3-methylbutoxy]phenyl]propionic acid; 3-[4-[3-[[[3-Methoxy-4-(5-oxazolyl)anilino]oxalyl]amino]-3-methylbutoxy]phenyl]propionic acid; 3-[2-[3-[[[3-Methoxy-4-(5-oxazolyl)anilino]oxalyl]amino]-3-methylbutoxy]phenyl]propionic acid; 2-[3-[3-[[[3-Methoxy-4-(5-oxazolyl)anilino]oxalyl]amino]-3-3-methylbutoxy]phenoxy]acetic acid; 4-[3-[[[3-Methoxy-4-(5-oxazolyl)anilino]oxalyl-amino]-3-methylbutoxy]-3-methylbenzoic acid; N-[3-(4-Cyano-2-methoxy phenoxy)-1,1-dimethylpropyl]-N-[3-methoxy-4-(5-oxazolyl)phenyl]ox al amide; N-[3-(3-Cyanophenoxy-1,1-dimethylpropyl]-N-[3-methoxy-4-(5-oxazolyl)phenyl]oxalamide; N-[3-[4-(4-Acetyl-1-piperazinyl)phenoxy]-1,1-dimethylpropyl]-N'-[3-methoxy-4-(5-oxazolyl)phenyl]oxalamide; N-[3-Methoxy-4-(5-oxazolyl)phenyl]-N'-[1,1-dimethyl-3-(2-morpholinophenoxyl)propyl]oxalamide; N-[3-Methoxy-4-(5-oxazolyl)phenyl]-N'-[1,1-dimethyl-3-[3-(dimethylamino)phenoxy]propyl]oxalamide; N-[3-(1,3-Benzodioxol-5-yloxy)-1,1-dimethylpropyl-N-[3-methoxy-4-(5-oxazolyl)phenyl]oxalamide; N-[3-Methoxy-4-(5-oxazolyl)phenyl]-N-[3-(3,4,5-trimethoxyphenoxy)-1,1-dimethylpropyl]oxalamide; N-[3-Methoxy-4-(5-oxazolyl)phenyl]-N'-[3-(3,5-dimethoxyphenoxy)-1,1-dimethylpropyl]oxalamide; N-[3-(5,6,7,8-Tetrahydro-5-oxo-2-naphthyloxy)-1,1-dimethylpropyl]-N'-(3-methoxy-4-(5-oxazolyl)phenyl]oxalamide; N-[3-(2-Acetamido-5-methylphenoxy)-1,1-dimethylpropyl]-N'-[3-methoxy-4-(5-oxazolyl)phenyl]oxalamide; N-[3-(3-Acetamidophenoxy)-1,1-dimethylpropyl]-N'[3-methoxy-4-(5-oxazolyl)phenyl]oxalamide; N-[3-(1H-Indol-4-yloxy)-1,1-dimethylpropyl]-N-[3-methoxy-4-(5-oxazolyl)phenyl]oxalamide; N-[3-(2-Fluoro-6-methoxyphenoxy)-1,1-dimethylpropyl]-N-[3-methoxy-4-(5-oxazolyl)phenyl]oxalamide; N-[3-Methoxy-4-(5-oxazolyl)phenyl]-N'-[1,1-dimethyl-3-2-oxo-2H-1-benzopyran-7-yloxy)propyl]oxalamide; N-[3-(4-Acetyl-3-methylphenoxy)-1,1-dimethylpropyl]-N-[3-methoxy-4-(5-oxazolyl)phenyl]oxalamide; (E)-N-[3-Methoxy-4-(5-oxazolyl)phenyl]-N'41,1-dimethyl-3-[4-(3-oxo-1-butenyl)phenoxy]propyl]oxalamide; N-[3-(3-Acetylphenoxy)-1,1-dimethylpropyl]-N'-[3-methoxy-4-(5-oxazolyl)phenyl]oxalamide; N-[3-(4-Acetylphenoxy)-1,1-dimethylpropyl]-N'-[3-methoxy-4-(5-oxazolyl)phenyl]oxalamide; N-[3-(4-Acetamido-2-chlorophenoxy)-1,1-dimethylpropyl]-N'-[3-methoxy-4-(5-oxazolyl)phenyl]oxalamide; N-[3-Methoxy-4-(5-oxazolyl)phenyl]-N'-[1,1-dimethyl-3-(4-pyridyloxy)propyl]oxalamide; N-[3-Methoxy-4-(5-oxazolyl)phenyl]-N'-[1,1-dimethyl-3-(1-oxido-4-pyridyloxy)propyl]oxalamide; N-[3-Methoxy-4-(5-oxazolyl)phenyl]-N'-[1,1-dimethyl-3-(2,6-dimethyl-4-pyridyloxy)propyl]oxalamide; N-[3-Methoxy-4-(5-oxazolyl)phenyl]-N'-[1,1-dimethyl-3-(2,6-dimethyl-1-oxido-4-pyridyloxy)propyl]oxalamide; N-[2-(4-Cyanophenoxy)-1,1-dimethylethyl]-N'-(3-methoxy-4-(5-oxazolyl)phenyl]oxalamide; N-[3-Methoxy-4-(5-oxazolyl)phenyl]-N'-[3-(2-methoxy-4-pyridyloxy)-1,1-dimethylpropyl]oxalamide; N-[3-Methoxy-4-(5-oxazolyl)phenyl]-N'-[1,1-dimethyl-2-[4-(1H-tetrazol-5-yl)phenoxy]ethyl]oxalamide; N-[3-(4-Cyanophenoxy)-1,1-dimethylpropyl]-N'-[3-methoxy-4-(5-oxazolyl)phenyl]oxalamide; N-[2-(3-Cyanophenoxy)-1,1-dimethylethyl]-N'-[3-methoxy-4-(5-oxazolyl)phenyl]oxalamide; N-[3-Methoxy-4-(5-oxazolyl)phenyl]-N'-[1,1-dimethyl-2-[3-(1H-tetrazol-5-yl)phenoxy]ethyl]oxalamide; N-[3-Methoxy-4-(5-oxazolyl)phenyl]-N'-[1,1-dimethyl-3-[4-(1H-tetrazol-5-yl)phenoxy]propyl]oxalamide; Benzyl 2-methoxy-4-[3-[[[3-methoxy-4-(5-oxazolyl)anilino]oxalyl]amino]-3-methylbutoxy]benzoate; 3-Chloro-4-[3-[[[3-methoxy-4-(5-oxazolyl)anilino]oxalyl)amino]-3-methylbutoxy]benzoic acid; 2-Methoxy-4-[3-3-methoxy-4-(5-oxazolyl)anilino]oxalyl]amino]-3-methylbutoxy]benzoic acid; 3-Methoxy-4-[3-[[[3-methoxy-4-(5-oxazolyl)anilino]oxalyl]amino]-3-methylbutoxy]benzoic acid; 2-Chloro-4-[3-[[[3-methoxy-4-(5-oxazolyl)anilino]oxalyl)amino]-3-methylbutoxy-benzoic acid; 4-[3-[[[3-Methoxy-4-(5-oxazolyl)anilino]oxalyl]amino]-3-methylbutoxy]-2-quinolinecarboxylic acid; (cis/trans)-4-[3-[[[3-Methoxy-4-(5-oxazolyl)anilino]oxalyl]amino]-3-methylbutoxy]-1-cyclohexanecarboxylic acid; (cis/trans)-4-[2-[[[3-Methoxy-4-(5-oxazolyl)anilino]oxalyl]amino]-2-methylpropoxy]-1-cyclohexanecarboxylic acid; 3-Fluoro-4-[3-[[[3-methoxy-4-(5-oxazolyl)anilino]oxalyl]amino]-3-methylbutoxy)benzoic acid; 3-Acetamido-4-[3-[[[3-methoxy-4-(5-oxazolyl)anilino)oxalyl]amino]-3-methylbutoxy]benzoic acid; 3-(Methanesulfonamido)-4-[3-[[[3-methoxy-4-(5-oxazolyl)anilino]oxalyl]amino]-3-methylbutoxy]benzoic acid; 4-[3-[[[3-Methoxy-4-(5-oxazolyl)anilino]oxalyl]amino]-3-methylbutoxy]-3,5-dimethylbenzoic acid; 3-[3-[[[3-Methoxy-4-(5-oxazolyl)anilino]oxalyl)amino]-3-methylbutoxy]-2-pyridinecarboxylic acid; 8-[3-[[[3-Methoxy-4-(5-oxazolyl)anilino]oxalyl]amino]-3-methylbutoxy]-2-quinolinecarboxylic acid; 5-[3-[[[3-Methoxy-4-(5-oxazolyl)anilino)oxalyl]amino]-3-methylbutoxy]-2-indolecarboxylic acid; N-Cyano-N"-cyclohexyl-N"-[3-methoxy-4-(5-oxazolyl)phenyl]guanidine; N-Cyano-N'-(1-cyclohexylethyl)-N"-[3-methoxy-4-(5-oxazolyl)-phenyl]guanidine; N-Cyano-N'-[3-methoxy-4-(5-oxazolyl)phenyl]-N"-propylguanidine; N-Cyano-N'-(2,3-dihydro-1H-inden-2-yl)-N"-[3-methoxy-4-(5-oxazolyl)-phenyl]guanidine; N-Cyano-N'-cyclopentyl-N"-[3-methoxy-4-(5-oxazolyl)phenyl]guanidine; N-Cyano-N'[3-methoxy-4-(5-oxazolyl)phenyl]-N"-[(5-methyl-2-furanyl)methyl]guanidine; N-Cyano-N-[3-methoxy-4-(5-oxazolyl)phenyl]-N"-(2-thienylmethyl)-guanidine; N-Cyano-N'-[3-methoxy-4-(5-oxazolyl)phenyl]-N"-[(2-methylphenyl)-methyl]guanidine; N-Cyano-N'-[3-methoxy-4-(5-oxazolyl)phenyl]-N"-[(3-methylphenyl)-methyl]guanidine; N-[(2-Bromophenyl)methyl]-N'-cyano-N"-[3-methoxy-4-(5-oxazolyl)-phenyl]guanidine; N-[(4-Chlorophenyl)methyl]-N'-cyano-N"-[3-methoxy-4-(5-oxazolyl)phenyl]guanidine; N-(Bicyclo[2.2.1]heptan-2-yl)-N'-cyano-N"-[3-methoxy-4-(5-oxazolyl)-phenyl]guanidine; N-Cyano-N'-[3-methoxy-4-(5-oxazolyl)phenyl]-N"'-(4-methylcyclohexyl)-guanidine; N-Cyano-N-[3-methoxy-4-(5-oxazolyl)phenyl]-N"-(3-methylbutyl)-guanidine; N-[(4-Aminophenyl)methyl]-N'-cyano-N'-[3-methoxy-4-(5-oxazolyl)-phenyl]guanidine; N-Cyano-N'-(cyclopropylmethyl)-N"-[3-methoxy-4-(5-oxazolyl)phenyl]-guanidine; N-Butyl-N-cyano-N"-[3-methoxy-4-(5-oxazolyl)phenyl]guanidine; N-[(3-Chlorophenyl)methyl]-N-cyano-N"-[3-methoxy-4-(5-oxazolyl)-phenyl]guanidine; N-Cyano-N'-[4-(1,1-dimethylethyl)cyclohexyl]-N'-[3-methoxy-4-(5-oxazolyl)phenyl]guanidine; N-Cyano-N'-(3-methoxy-4-(5-oxazolyl)phenyl]-N"-phenylguanidine; N-Cyano-N'-(3-methoxy-4-(5-oxazolyl)phenyl)-N"-(2-methylphenyl)-guanidine; N-Cyano-N-(3-methoxy-4-(5-oxazolyl)phenyl)-N"-(4-methylphenyl)-guanidine; N-Cyano-N'-[3-methoxy-4-(5-oxazolyl)phenyl]-N"-[3-(1-methylethyl)phenyl]guanidine; N-Cyano-N-[3-methoxy-4-(5-oxazolyl)phenyl]-N"-[3-(trifluoromethoxy)-phenyl]guanidine; N-Cyano-N'-[3-(1,1-dimethylethyl)phenyl]N"-[3-methoxy-4-(5-oxazolyl)phenyl]guanidine; N-Cyano-N'-[3-methoxy-4-(5-oxazolyl)phenyl]-N"-[3-(2-phenoxyethoxy)phenyl]guanidine; N-Cyano-N'-[3-(hydroxymethyl)

phenyl]-N"-[3-methoxy-4-(5-oxazolyl)phenyl]guanidine; N-Cyano-N'-[3-methoxy-4-(5-oxazolyl)phenyl]-N"-(2-phenylcyclopropyl)guanidine; N-Cyano-N'[3-methoxy-4-(5-oxazolyl)phenyl]-N"-3-pyridinylguanidine; [[3-[[[(Cyanoamino)[[3-methoxy-4-(5-oxazolyl)phenyl]amino]methylene]amino]phenyl]methyl]carbamic acid tetrahydro-3-furanyl ester; [[3-[[[(Cyanoamino)[[3-methoxy-4-(5-oxazolyl)phenyl]amino]methylene]amino]phenyl]methyl]carbamic acid tetrahydro-3-furanylmethyl ester; N-[3-[[[(Cyanoamino)phenoxymethylene]amino]methyl]phenyl]-N-[3-methoxy-4-(5-oxazolyl)phenyl]urea; N-[3-[[[Amino(cyanoamino)methylene]amino]methyl]phenyl]-N'-[3-methoxy-4-(5-oxazolyl)phenyl]urea; N-[3-[[[(Cyanoamino)(4-morpholinyl)methylene]amino]methyl]phenyl]-N'-[3-methoxy-4-(5-oxazolyl)phenyl]urea; N-[3-[[[(Cyanoamino)[[2-(1H-imidazol-4-yl)ethyl]amino]methylene]-amino]methyl]phenyl]-N'-[3-methoxy-4-(5-oxazolyl)phenyl]urea; N-[3-[[[(Cyanoamino)(4-hydroxy-1-piperidinyl)methylene]amino]-methyl]phenyl]-N'-[3-methoxy-4-(5-oxazolyl)phenyl]urea; N-[3-[[[(Cyanoamino)(3-hydroxy-1-piperidinyl)methylene]amino]-methyl]phenyl]-N-[3-methoxy-4-(5-oxazolyl)phenyl]urea; N-[3-[[[(Cyanoamino)(cyclohexylamino)methylene amino]methyl]-phenyl]-N'-[3-methoxy-4-(5-oxazolyl)phenyl]urea; N-[3-[[[(Cyanoamino)[(4-pyridinylmethyl)amino]methylene]amino]-methyl]phenyl]-N'-[3-methoxy-4-(5-oxazolyl)phenyl]urea; N-[3-[[[(Cyanoamino)[[(tetrahydro-2-furanyl)methyl]amino]methylene]-amino]methyl]phenyl]-1V-[3-methoxy-4-(5-oxazolyl)phenyl]urea; N-[3-[[[(Cyanoamino)[4-(2-hydroxyethyl)-1-piperazinyl]methylene]-amino methyl]phenyl]-N-[3-methoxy-4-(5-oxazolyl)phenyl]urea; N-[3-[[[(Cyanoamino)(methylamino)methylene amino]methyl]phenyl]-N'-[3-methoxy-4-(5-oxazolyl)phenyl]urea; (R)—N-[3-[[[(Cyanoamino)[(tetrahydro-2-furanylmethyl)amino]-methylene]amino]methyl]phenyl]-N'-[3-methoxy-4-(5-oxazolyl)phenyl]urea; (S)—N-[3-[[[(Cyanoamino)[(tetrahydro-2-furanylmethyl)amino]-methylene]amino]methyl]phenyl]-N'-[3-methoxy-4-(5-oxazolyl)phenyl]urea; N-[3-[[[(Cyanoamino)[(tetrahydro-2-furanyl)methoxy]methylene]amino]-methyl]phenyl]-N-[3-methoxy-4-(5-oxazolyl)phenyl]urea; N-[3-[[[(Cyanoamino)methoxymethylene]amino]methyl]phenyl]-N'-[3-methoxy-4-(5-oxazolyl)phenyl]urea; N-[3-[[[(Cyanoamino) [(tetrahydro-3-furanyl)methoxy]methylene]amino]-methyl]phenyl]-N'-[3-methoxy-4-(5-oxazolyl)phenyl]urea; N-[3-[[Amino(cyanoamino)methylene]amino]phenyl]-N'-[3-methoxy-4-(5-oxazolyl)phenyl]urea; N-(4-Fluorophenyl)-N2-[3-methoxy-4-(5-oxazolyl)phenyl]glycinamide; N-[3-Methoxy-4-(5-oxazolyl)phenyl]-N2-phenylglycinamide; N-[3-Methoxy-4-(5-oxazolyl)phenyl]-N2-(3-methylphenyl)glycinamide; N-[3-Methoxy-4-(5-oxazolyl)phenyl]-N'-phenylethanediamide; N-[3-Methoxy-4-(5-oxazolyl)phenyl]-N'-(2-methylphenyl)ethanediamide; N-[3-Methoxy-4-(5-oxazolyl)phenyl]-N'-(3-methylphenyl)ethanediamide; N-[3-Methoxy-4-(5-oxazolyl)phenyl]-N'-(4-methylphenyl)ethanediamide; (S)-[[3-[[[[3-Methoxy-4-(5-oxazolyl)phenyl]amino]oxoacetyl]amino]phenyl]methyl]carbamic acid tetrahydro-3-furanyl ester; N-[3-Methoxy-4-(5-oxazolyl)phenyl]-N'-(3-methoxyphenyl)ethane diamide; N-[3-Methoxy-4-(5-oxazolyl)phenyl]-N'-(phenylmethyl)ethanediamide; N-(4-Cyanophenyl)-N'-[3-methoxy-4-(5-oxazolyl)phenyl]ethanediamide; N-[3-Methoxy-4-(5-oxazolyl)phenyl]-N'-(3-methylphenyl)propanediamide; N-[3-Methoxy-4-(5-oxazolyl)phenyl]-N'-(phenyl)propanediamide; (S)-[[3-[[3-Methoxy-4-(5-oxazolyl)phenyl]amino]-1,3-dioxopropyl]amino]phenyl]methyl] carbamic acid tetrahydro-3-furanyl ester; N-(1,1-Dimethylethyl)-N'[3-methoxy-4-(5-oxazolyl)phenyl]ethanediamide; N'-[1,1-Bis(hydroxymethyl)propyl]-N-[3-methoxy-4-(5-oxazolyl)phenyl]ethanediamide; N-(2-Hydroxy-1,1-dimethylethyl)-N'-[3-methoxy-4-(5-oxazolyl)phenyl]ethanediamide; N-[[[3-Methoxy-4-(5-oxazolyl)phenyl]amino]oxoacetyl]-2-methylalanine 1,1-dimethylethyl ester; N-(2-Hydroxy-1,1-dimethylpentyl)-N'-[3-methoxy-4-(5-oxazolyl)phenyl]ethanediamide; N-[2-[(2-Hydroxy-1,1-dimethylethyl)amino]-1,1-dimethylethyl]-N-[3-methoxy-4-(5-oxazolyl)phenyl]ethanediamide; N-[2-(Dimethylamino)-1,1-dimethylethyl-N'-[3-methoxy-4-(5-oxazolyl)phenyl]ethanediamide; N-(1,1-Diethyl-2-propynyl)-N'-[3-methoxy-4-(5-oxazolyl)phenyl]ethanediamide; N-[3-Methoxy-4-(5-oxazolyl)phenyl]-N'-(1,1,3,3-tetramethylbutyl)ethanediamide; N-(1,1-Dimethylpropyl)-N'-[3-methoxy-4-(5-oxazolyl)phenyl]ethanediamide; N-[1-(Hydroxymethyl)cyclopentyl]-N'-[3-methoxy-4-(5-oxazolyl)phenyl]ethanediamide; N-[2-(4-Fluorophenyl)-1,1-dimethyl ethyl]-N'-[3-methoxy-4-(5-oxazolyl)phenyl]ethanediamide; N-[[[3-Methoxy-4-(5-oxazolyl)phenyl]amino]oxoacetyl]-.alpha.-methyltyrosine methyl ester; N-[[[3-Methoxy-4-(5-oxazolyl)phenyl]amino]oxoacetyl]-.alpha.-methyltryptophan methyl ester; N'-[1,1-Bis(hydroxymethyl)ethyl]-N-[3-methoxy-4-(5-oxazolyl)phenyl]-N-methylethanediamide; N-(1,1-Dimethyl-3-oxobutyl)-N'-[3-methoxy-4-(5-oxazolyl)phenyl]ethanediamide; N-[3-Methoxy-4-(5-oxazolyl)phenyl]-N'-(1-methyl-1-phenylethyl)ethanediamide; N-[[[3-Methoxy-4-(5-oxazolyl)phenyl]amino]oxoacetyl]-2-methylalanine methyl ester; 1-[[[[3-Methoxy-4-(5-oxazolyl)henyl]amino]oxoacetyl]amino]cyclopropanecarboxylic acid methyl ester; N-(1-Ethynylcyclohexyl)-N'[3-methoxy-4-(5-oxazolyl)phenyl]ethanediamide; (R)—N-[1-(Hydroxymethyl)-1-methylpropyl]-N'[3-methoxy-4-(5-oxazolyl)phenyl]-N-methylethanediamide; $N^3$-[3-Methoxy-4-(5-oxazolyl)phenyl]-1-phenyl-1H-1,2,4-tirazole-3,5-diamine; $N^3$-[3-Methoxy-4-(5-oxazolyl)phenyl]-1-(2-methylphenyl)-1H-1,2,4-triazole-3,5-diamine; $N^3$-[3-Methoxy-4-(5-oxazolyl)phenyl]-1-(3-methylphenyl)-1H-1,2,4-triazole-3,5-diamine; 1-(4-Aminophenyl)$N^3$-[3-methoxy-4-(5-oxazolyl)phenyl]-1H-1,2,4-triazole-3,5-diamine; 1-(3-Aminophenyl)-$N^3$-[3-methoxy-4-(5-axazolyl)phenyl]-1H-1,2,4-triazole-3,5-diamine; 1-(3-Fluorophenyl)-$N^3$-[3-methoxy-4-(5-oxazolyl)phenyl]-1H-1,2,4-triazole-3,5-diamine; $N^3$-[5-Amino-3-[[3-methoxy-4-(5-oxazolyl)phenyl]amino]-1H-1,2,4-triazol-1-yl]benzonitrile; $N^3$-[3-Methoxy-(5-axazolyl)phenyl]-1-[4-(methylsulfonyl)phenyl]-1H-1,2,4-triazole-3,5-diamine; N-[3-Methoxy-4-(5-oxazolyl)phenyl]-5-phenyl-1H-1,2,4-triazol-3-amine; N-[3-Methoxy-4-(5-oxazolyl)phenyl]-5-phenyl-1,3,4-oxadiazol-2-amine; N-[3-Methoxy-4-(5-oxazolyl)phenyl]-5-phenyl-1,3,4-thiadiazol-2-amine; N-[3-Methoxy-4-(5-oxazolyl)phenyl]-5-phenyl-2-oxazolamine; N-[3-Methoxy-4-(5-oxazolyl)phenyl]-4-methyl-5-phenyl-2-oxazolamine; N-[3-Methoxy-4-(5-oxazolyl)phenyl]-5-(2-methoxyphenyl)-2-oxazolamine; N-[3-Methoxy-4-(5-oxazolyl)phenyl]-5-(4-methylphenyl)-2-oxazolamine; N-[3-Methoxy-4-(5-oxazolyl)phenyl]-5-(3-methylphenyl)-2-oxazolamine; N-[3-Methoxy-4-(5-oxazolyl)phenyl]-5-(2-methylphenyl)-2-oxazolamine; 4-Ethyl-N-[3-methoxy-4-(5-oxazolyl)phenyl]-5-phenyl-2-oxazolamine; N-[2-2-[[3-Methoxy-4-(5-oxazolyl)phenyl]amino]-5-oxazolyl]phenyl]-N-acetamide; N-[2-2-[[3-Methoxy-4-(5-oxazolyl)phenyl]amino]-5-oxazolyl]phenyl]-N-methylacetamide; N-[3-Methoxy-4-(5-oxazolyl)phenyl]-5-methyl-4-phenyl-2-oxazolamine; 2-Methoxy-N-[2-2-[[3-methoxy-4-(5-oxazolyl)phenyl]amino]-5-oxazolyl]phenyl]acetamide; N-[2-2-[[3-Methoxy-4-(5-oxazolyl)phenyl)amino]-5-oxazolyl]phenyl]-4-morpholineacetamide; 2-Methoxy-N-[2-[2-[[3-methoxy-4-(5-oxazolyl)phenyl]amino]-5-oxazolyl]phenyl]-N-methylacetamide; 2-Methoxy-N-[2-[2-[[3-methoxy-4-(5-oxazolyl)phenyl]amino]-5-oxazolyl]phenyl]-N-methylacetamide; [2-[2-[[3-Methoxy-4-(5-oxazolyl)phenyl]amino]-5-oxazolyl]phenyl]carbamic acid tetrahydro-3-furanyl ester; [2-[2-[[3-Methoxy-4-(5-oxazolyl)phenyl]amino]-5-oxazolyl]phenyl]methyl carbamic acid tetrahydro-3-furanyl ester; [2-[2-[[3-Methoxy-4-(5-oxazolyl)phenyl]amino]-5-oxazolyl]phenyl]methylcarbamic acid phenylmethyl ester; 2-[2-[[3-Methoxy-4-(5-oxazolyl)phenyl]amino]-5-oxazolyl]-N,N-dimethylbenzamide; N-[2-[2-[[3-Methoxy-4-(5-oxazolyl)phenyl]amino]-5-oxazolyl]phenyl]-N-methyl-4-morpholinepropanamide; N-[2-[2-[[3-Methoxy-4-(5-oxazolyl)phenyl]amino]-5-oxazolyl]phenyl]-$N,N^2,N^2$-trimethylglycinamide; N-[2-[2-[[3-Methoxy-4-(5-oxazolyl)phenyl]amino]-5-oxazolyl]phenyl]-$N,N^2$-dimethylglycinamide; N-[2-[2-[[3-Methoxy-4-(5-oxazolyl)phenyl]amino]-5-oxazolyl]phenyl]-N4-dimethyl-1-piperazineacetamide; N-[2-[2-[[3-Methoxy-4-(5-oxazolyl)phenyl]amino]-5-oxazolyl]phenyl]-N-methyl1H-1,2,4-triazole-1-acetamide; $N^2$-(1,1-Dimethylethyl)-N-[2-[2-[[3-methoxy-4-(5-oxazolyl)phenyl]amino]-5-oxazolyl]phenyl]-N-methylglycinamide; N-[2-[2-[[3-Methoxy-4-(5-oxazolyl)phenyl]amino]-5-oxazolyl]phenyl]-N-methyl-N2-(1-methylethyl)glycinamide; N-[2-[2-[[3-Methoxy-4-(5-oxazolyl)phenyl]amino]-5-oxazolyl]phenyl]-N-methyl-1H-imidazole-1-acetamide; N-[2-[2-[[3-Methoxy-4-(5-oxazolyl)phenyl]amino]-5-oxazolyl]phenyl]-N-methyl-1H-pyrazole-1-acetamide; N-[2-[2-[[3-Methoxy-4-(5-oxazolyl)phenyl]amino]-5-oxazolyl]phenyl]-N-methyl-2H-1,2,3-triazole-2-acetamide; N-[2-[2-[[3-Methoxy-4-(5-oxazolyl)phenyl]amino]-5-oxazolyl]phenyl]-N-methyl-1H-1,2,3-triazole-1-acetamide; N-[2-[2-[[3-Methoxy-4-(5-oxazolyl)phenyl]amino]-5-oxazolyl]phenyl]-N,.alpha.-dimethyl-4-morpholineacetamide; N-[2-[2-[[3-Methoxy-4-(5-oxazolyl)phenyl]amino]-5-oxazolyl]phenyl]-N-methyl-2-pyrrolidinecarboxamide; N-[2-[2-[[3-Methoxy-4-(5-oxazolyl)phenyl]amino]-5-oxazolyl]phenyl]-N-methyl-4-morpholineacetamide; N-[3-Methoxy-4-(5-oxazolyl)phenyl]-5-(3-nitrophenyl)-2-oxazolamine; 2-[2-[3-Methoxy-4-(5-oxazolyl)phenyl]amino]-5-oxazolyl]-N-methylbenzamide; (S)-2-[2-[[3-Methoxy-4-(5-oxazolyl)phenyl]amino]-5-oxazolyl]-N-(tetrahydro-3-furanyl) benzamide; 1-[[2-[2-[[3-Methoxy-4-(5-oxazolyl)phenyl]amino]-5-oxazolyl]phenyl]carbonyl]-4-methylpiperazine; 2-[2-[[3-Methoxy-4-(5-oxazolyl)phenyl]amino]-5-oxazolyl]-N-[2-(4-morpholinyl)ethyl]benzamide; 2-[2-[[3-Methoxy-4-(5-oxazolyl)phenyl]amino]-5-oxazolyl]-1-pyrrolidinecarboxylic acid ethyl ester; 4-Methoxy-N-[3-methoxy-4-(5-oxazolyl)phenyl]-6-phenyl-1,3,5-triazin-2-amine; N-[3-Methoxy-4-(5-oxazolyl)phenyl]-4-(4-phenyl-1-piperazinyl)-6-phenyl-1,3,5-triazin-2-amine; N-[3-Methoxy-4-(5-oxazolyl)phenyl]-4-(4-morpholinyl)-6-phenyl-1,3,5-triazin-2-amine; N-[3-Methoxy-4-(5-oxazolyl)phenyl]-6-phenyl-N'-(phenylmethyl)-1,3,5-triazine-2,4-diamine; N-[3-Methoxy-4-(5-oxazolyl)phenyl]-4-(4-methyl-1-piperazinyl)-6-phenyl-1,-3,5-triazin-2-amine; N-[3-Methoxy-4-(5-oxazolyl)phenyl]-6-phenyl-N'-(3-pyridylmethyl)-1,3,5-triazine-2,4-diamine; N-[3-Methoxy-4-(5-oxazolyl)phenyl]-N'-[(5-methyl-2-furanyl)methyl]-6-phenyl-1,3,5-triazine-2,4-diamine; N-[3-Methoxy-4-(5-oxazolyl)phenyl]-6-phenyl-N'-[2-(3-pyridinyl)ethyl]-1,3,5-triazine-2,4-diamine; N-[3-Methoxy-4-(5-oxazolyl)phenyl]-6-phenyl-N'-[(tetrahydro-2-furanyl)methyl]-1,3,5-triazine-2,4-diamine; N-[3-(1H-Imidazol-1-yl)propyl]-N-[3-methoxy-4-(5-oxazolyl)phenyl]-6-phenyl-1,3,5-triazine-2, 4-diamine; N-[3-Methoxy-4-(5-oxazolyl)phenyl]-6-phenyl-N'-[2-(4-pyridinyl)ethyl]-1,3,5-triazine-2,4-diamine; N-[[3-Methoxy-4-(5-oxazolyl)phenyl]amino]-6-phenyl-1,3,5-triazin-2-yl-]amino]-1-butanol; N-[3-Methoxy-4-(5-oxazolyl)phenyl]-6-phenyl-N'-(2-pyridinylmethyl)-1,3,5-triazine-2,4-diamine; N-[2-[[4-[[3-Methoxy-4-(5-oxazolyl)phenyl]amino]-6-phenyl-1,3,5-triazin-2-yl]amino]ethyl]acetamide; N-[3-Methoxy-4-(5-oxazolyl)phenyl]-N'-methylbutyl)-6-phenyl-1,3,5-triazine-2,4-diamine; N-[3-Methoxy-4-(5-oxazolyl)phenyl]-6-phenyl-1,3,5-triazine-2,4-diamine; N-Methoxy-N-[3-methoxy-4-(5-oxazolyl)phenyl]-6-phenyl-1,3,5-triazine-2,4-diamine; N-Butyl-N'[3-methoxy-4-(5-oxazolyl)phenyl]-6-phenyl-1,3,5-triazine-2,4-diamine; N-[2-(1H-Imidazol-4-yl)ethyl]-N'-[3-methoxy-4-(5-oxazolyl)phenyl]-6-phenyl-1-1,3,5-triazine-2,4-diamine; N-(2-Furanylmethyl)-N-[3-methoxy-4-(5-oxazolyl)phenyl]-6-phenyl-1,3,5-triazine-2,4-diamine; 2-[[4-[[3-Methoxy-4-(5-oxazolyl)phenyl]amino]-6-phenyl-1,3,5-triazin-2-yl-]propylamino]ethanol; N-[3-Methoxy-(5-oxazolyl)phenyl]-6-phenyl-N'-(4-pyridinylmethyl)-1,3,5-triazine-2,4-diamine; (S)-1-[4-[[3-Methoxy-4-(5-oxazolyl)phenyl]amino]-6-phenyl-1,3,5-triazin-2-yl]-2-pyrrolidinemethanol; 4-[4-[[3-Methoxy-4-(5-oxazolyl)phenyl]amino]-6-phenyl-1,3,5-triazin-2-yl]-1-piperazinecarboxaldehyde; 1-[4-[[3-Methoxy-4-(5-oxazolyl)phenyl]amino]-6-phenyl-1,3,5-triazin-2-yl]-4-piperidineethanol; N-[2-(Dimethylamino)ethyl]-N-ethyl-N-[3-methoxy-4-(5-oxazolyl)phenyl]-6-phenyl-1,3,5-triazine-2,4-diamine; 1'-[4-[[3-Methoxy-4-(5-oxazolyl)phenyl]amino]-6-phenyl-1,3,5-triazin-2-yl]-1-piperidineethanol; 1-[4-[[3-Methoxy-4-(5-oxazolyl)phenyl]amino]-6-phenyl-1,3,5-triazin-2-yl]-4-piperidinol; N-[1-[4-[[3-Methoxy-4-(5-oxazolyl)phenyl]amino]-6-phenyl-1,3,5-triazin-2-yl]-3-pyrrolidinyl]acetamide; 2-[[4-[[3-Methoxy-4-(5-oxazolyl)phenyl]amino]-6-phenyl-1,3,5-triazin-2-yl](phenylmethyl)amino]ethanol; 1-[4-[[3-Methoxy-4-(5-oxazolyl)phenyl]amino]-6-phenyl-1,3,5-triazin-2-yl]-L-prolinamid 1-[4-[[3-Methoxy-4-(5-oxazolyl)phenyl]amino]-6-phenyl-1,3,5-triazin-2-yl]-3-pyrrolidinol; (S)-4-[2-(Methoxymethyl)-1-pyrrolidinyl]-N-[3-methoxy-4-(5-oxazolyl)pheny-l]-6-phenyl-1,3,5-triazin-2-amine; 4-[[4-[[3-Methoxy-4-(5-oxazolyl)phenyl]amino]-6-phenyl-1,3,5-triazin-2-yl-]amino]butanoic acid; N-1-[[4-[[3-Methoxy-4-(5-oxazolyl)phenyl]amino]-6-phenyl-1,3,5-triazin-2-yl-]oxy]-2-propanol; 2-[[4-[[3-Methoxy-4-(5-oxazolyl)phenyl]amino]-6-phenyl-1,3,5-triazin-2-yl-]amino]-1,3-propanediol; 2-[[3-Methoxy-4-(5-oxazolyl)phenyl]amino]-6-phenyl-4(3H)-triazinone; N-[2-[2-[[3-Methoxy-4-(5-oxazolyl)phenyl]amino]-5-oxazolyl]phenyl]-N-methyl-1-piperidineacetamide; (S)-2-(Methoxymethyl)-N-[2-[2-[[3-methoxyl-4-(5-oxazolyl)phenyl]amino]-5-oxazolyl]phenyl]-N-methyl-1-pyrrolidineacetamide; 2-Amino-N-[2-[2-[[3-methoxy-4-(5-oxazolyl)phenyl]amino]-5-oxazolyl]phenyl-]-N-methylacetamide; N-[2-[2-[[3-Methoxy-4-(5-oxazolyl)phenyl]amino]-5-oxazolyl]phenyl]-N2-dimethyipropanamide; N-[2-[2-[[3-Bromo-4-(5-oxazolyl)phenyl]amino]-5-oxazolyl]phenyl]-N-methyl-4-morpholineacetamide; N-[2-[2-[[3-Chloro-4-(5-oxazolyl)phenyl]amino]-5-oxazolyl]phenyl]-N-methy-1-4-morpholineacetamide; 2-Hydroxy-N-[2-[2-[[3-methyl-4-(5-oxazolyl)phenyl]amino]-5-oxazolyl]pheny-1]-N-methylacetamide; N-Methyl-N-[2-[2-[[3-methyl-4-(5-oxazolyl)phenyl]amino]-5-oxazolyl]phenyl-morpholineacetami de; N-[3-Methoxy-4-(1H-1,2,4-triazol-1-yl)phenyl]-5-phenyl-2-oxazolamine; and N-[3-Methoxy-4-cyanophenyl]-5-phenyl-2-oxazolamine.

Additional compounds utilized in the present invention as inhibitors of angiogenesis, and utilized to treat diseases or disorders associated with angiogenesis include, but are by no means limited to the following compounds traditionally known 20 to those of ordinary skill in the art as anti-fungal compounds: 1-[2-(2,4-dichlorophenyl)-2-[(2,4-dichlorophenyl)methoxy]ethyl]-1H-imidazole; 3-(4-amino-3,5-dihydroxy-6-methyl-tetrahydropyran-2-yl)oxy-19,25,27,30,31,33,35,37-octahydroxy-18,20,21-trimethyl-23-oxo-22,39-dioxabicyclo[33.3.1]nonatriaconta-4,6,8,10,12,14,16-heptaene-38-carboxylic acid; 1-[(2-chlorophenyl)-diphenylmethyl]-1H-imidazole; 4-[2-[(4-chlorophenyl)methoxy]-2-(2,4-dichlorophenyl)-ethyl]-4H-imidazole; 1-[2-[(4-chlorophenyl)methoxy]-2-(2,4-dichlorophenyl)-ethyl]-1H-imidazole; 7-chloro-2',4,6-trimethoxy-6'-methyl-spiro[benzofuran-2(3H), 1'-cyclohex-2'-ene]-3,4'-dione; 7-chloro-2',4,6-trimethoxybenzofuran-2(3H)-spiro-1'-cyclohex-2'-ene-3,4'-dione; 7-chloro-4,6-dimethoxycoumaran-3-one-2-spiro-1'-(2'-methoxy-6'-methylcyclohex-2'-en-4'-one); 2-(2,4-difluorophenyl)-1,3-bis(1H-1,2,4-triazol-1-yl)propan-2-ol; 1-[4-[4-[[2-(2,4-dichlorophenyl)-2-(1H-imidazol-1-ylmethyl)-1,3-dioxolan-4-yl]methoxy]phenyl]piperazin-1-yl]ethanone; 1-[2-(2,4-dichlorophenyl)-2-[(2,4-dichlorophenyl)methoxy]ethyl]-1H-imidazole; 33-(4-amino-3,5-dihydroxy-6-methyl-tetrahydropyran-2-yl)oxy-1,3,4,7,9,11,17,37-octahydroxy-15,16,18-trimethyl-13-oxo-14,39-dioxabicyclo[33.3.1]nonatriaconta-19,21,25,27,29,31-hexaene-36-carboxylic acid; 4-[4-[4-[4-[[2-(2,4-dichlorophenyl)-2-(1H-1,2,4-triazol-1-ylmethyl)-1,3-dioxolan-4-yl]methoxy]phenyl]piperazin-1-yl]phenyl]-2-(1-methylpropyl)-2,4-dihydro-1,2,4-triazol-3-one; 2-(2,4-difluorophenyl)-3-(5-fluoropyrimidin-4-yl)-1-(1H-1,2,4-triazol-1-yl)butan-2-ol; 1-[(2-chlorophenyl)-diphenyl-methyl]-1H-imidazole; 4-amino-5-fluoro-3H-pyrimidin-2-one; N,6,6-trimethyl-N-(naphthalen-1-ylmethyl)hept-2-en-4-yn-1-amine; 1-[2-[(2-chlorothiophen-3-yl)methoxy]-2-(2,4-dichlorophenyl)-ethyl]-1H-imidazole; 1-[4-[[2-(2,4-dichlorophenyl)-2-(1H-1,2,4-triazol-1-ylmethyl)-1,3-dioxolan-4-yl]methoxy]phenyl]-4-(1-methylethyl) piperazine; 1-[4-(4-chlorophenyl)-2-(2,6-dichlorophenyl) sulfanyl-butyl]-1H-imidazole; 3-anilinoimino-5-imino-6-(4-nitrophenyl)aminoimino-4-oxo-naphthalene-2,7-disulfonic acid; 5-chloro-7-iodo-quinolin-8-ol; 6-cyclohexyl-1-hydroxy-4-methyl-1H-pyridin-2-one; 2-aminoethanol; [2-acetyloxy-1-(acetyloxymethyl)ethyl] ethanoate; N-methyl-N-(3-methylphenyl)-1-naphthalen-2-yloxy-methanethioamide; echinocandins, epoxytriazole derivatives, thiocarbamates, allylamines, caspofungin, Miconazole, Amphotericin B, Clotrimazole, Econazole, Griseofulvin, Fluconazole, Ketoconazole, Miconazole, Nystatin, Itraconazole, Voriconazole, Clotrimazole, Caspofungin, Allylamines, Thiocarbamates, 5-fluorocytosine, Flucytosine, Epoxytriazole derivatives, Terbinafine, Echinocandins, Tioconazole, Terconazole, Butoconazole Nitrate, Unecylenic Acid, Clioquinol, Ciclopirox Olamine, Econazole Nitrate, Triacetin, and Tolnaftate.

III. Pharmaceutical Compositions/Methods of Administration

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

While the angiogenesis inhibiting compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The angiogenesis inhibiting compounds of the present invention may be administered orally, parenterally, by inhalation spray, rectally, vaginally, or topically in dosage unit formulations containing conventional pharmaceutically acceptable carriers, adjuvants, and vehicles. The term parenteral as used herein includes, subcutaneous, intravenous, intramuscular, intrasternal, infusion techniques, intraperitoneally, eye or ocular, intrabuccal, transdermal, intranasal, into the brain, including intracranial and intradural, into the joints, including ankles, knees, hips, shoulders, elbows, wrists, directly into tumors, and the like, and in suppository form.

The pharmaceutically active compounds of this invention can be processed in accordance with conventional methods of pharmacy to produce medicinal agents for administration to patients, including humans and other mammals.

Modifications of the active compound can affect the solubility, bioavailability and rate of metabolism of the active species, thus providing control over the delivery of the active species. Further, the modifications can affect the anti-angiogenesis activity of the compound, in some cases increasing the activity over the parent compound. This can easily be assessed by preparing the derivative and testing its activity according to known methods well within the routineer's skill in the art.

Pharmaceutical compositions based upon these chemical compounds comprise the above-described compounds in a therapeutically effective amount for treating diseases and conditions which have been described herein, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The active compound is included in the pharmaceutically acceptable carrier or diluent in an amount sufficient to deliver to a patient a therapeutically effective amount for the desired indication, without causing serious toxic effects in the patient treated.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as algmic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material—of the above type, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or, granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of phaxmaceutically active ingredients, are known in the art and described in several issued U.S. patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as emylenediaminetetraacetic acid; buffers such as acetates, citrates or phosphates and agents for the adjustment of tonicity such as sodium chloride or dextrose.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

A skilled artisan will recognize that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up. to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Formulations suitable for parenteral administration include aqueous and nonaqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. "Where an organ or tissue is accessible because of removal from the patient, such organ or tissue may be bathed in a medium containing the subject compositions, the subject compositions may be painted onto the organ, or may be applied in any convenient way.

The angiogenesis-inhibiting compound may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

More specifically, the angiogenesis-inhibiting compound is administered through an ocular device suitable for direct implantation into the vitreous of the eye. Such devices of the present invention are surprisingly found to provide sustained controlled release of various compositions to treat the eye without risk of detrimental local and systemic side effects. An object of the present ocular method of delivery is to maximize the amount of drug contained in an intraocular device while minimizing its size in order to prolong the duration of the implant. See, e.g., U.S. Pat. Nos. 5,378,475; 5,773,019; 6,001,386; 6,217,895, 6,375,972, and 6,756,058 and U.S. Publications 20050096290 and 200501269448.

Other methods of delivery include: an ocular delivery system that could be applied to an intra-ocular lens to prevent inflammation or posterior capsular opacification, an ocular delivery system that could be inserted directly into the vitreous, under the retina, or onto the sclera, and wherein inserting can be achieved by injecting the system or surgically implanting the system, a sustained release drug delivery system, and a method for providing controlled and sustained administration of an agent effective in obtaining a desired local or systemic physiological or pharmacological effect comprising surgically implanting a sustained release drug delivery system at a desired location.

Examples include, but are not limited to the following: a sustained release drug delivery system comprising an inner reservoir comprising an effective amount of an agent effective in obtaining a desired local or systemic physiological or pharmacological effect, an inner tube impermeable to the passage of said agent, said inner tube having first and second ends and covering at least a portion of said inner reservoir, said inner tube sized and formed of a material so that said inner tube is capable of supporting its own weight, an impermeable member positioned at said inner tube first end, said impermeable member preventing passage of said agent out of said reservoir through said inner tube first end, and a permeable member positioned at said inner tube second end, said permeable member allowing diffusion of said agent out of said reservoir through said inner tube second end; a method for administering a compound of the invention to a segment of an eye, the method comprising the step of implanting a sustained release device to deliver the compound of the invention to the vitreous of the eye or an implantable, sustained release device for administering a compound of the invention to a segment of an eye; a sustained release drug delivery device comprising: a) a drug core comprising a therapeutically effective amount of at least one first agent effective in obtaining a diagnostic effect or effective in obtaining a desired local or systemic physiological or pharmacological effect; b) at least one unitary cup essentially impermeable to the passage of said agent that surrounds and defines an internal compartment to accept said drug core, said unitary cup comprising an open top end with at least one recessed groove around at least some portion of said open top end of said unitary cup; c) a permeable plug which is permeable to the passage of said agent, said permeable plug is positioned at said open top end of said unitary cup wherein said groove interacts with said permeable plug holding it in position and closing said open top end, said permeable plug allowing passage of said agent out of said drug core, through said permeable plug, and out said open top end of said unitary cup; and d) at least one second agent effective in obtaining a diagnostic effect or effective in obtaining a desired local or systemic physiological or pharmacological effect; or a sustained release drug delivery device comprising: an inner core comprising an effective amount of an agent having a desired solubility and a polymer coating layer, the polymer layer being permeable to the agent, wherein the polymer coating layer completely covers the inner core.

The methods are particularly suitable for treating ocular conditions such as glaucoma, proliferative vitreoretinopathy, macular edema, including diabetic macular edema, age-related macular degeneration, diabetic retinopathy, uveitis, ocular neovascularization, and ocular infection. The devices are also particularly suitable for use as an ocular device in treating subjects suffering from ocular histoplasmosis, wherein the device is surgically implanted within the vitreous of the eye.

The angiogenesis-inhibiting compound may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prednisone, dexamethasone), non-steroidal anti-inflammatory drugs (NSAIDS) (e.g., ibuprofen, celecoxib, aspirin, indomethicin, naproxen), alkylating agents such as busulfan, cis-platm, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

The active compound or pharmaceutically acceptable salts thereof can also be mixed with other active materials that do not impair the desired action, or with materials that supplement the desired action, such as other anticancer agents, and in certain instances depending upon the desired therapy or target, antibiotics, antifungals, antinflammatories, antiviral compounds or other agents having a distinct pharmacological effect.

Alternatively, the compound of the invention may be administered apart from the at least one known cancer chemotherapeutic agent. In one embodiment, the compound of the invention and the at least one known cancer chemotherapeutic agent are administered substantially simultaneously, i.e., the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

It should be understood that in addition to the ingredients particularly mentioned above, the formulations of the present invention may include other agents conventional in the art having regard to the type of formulation in question, for example, those suitable for oral administration may include flavoring agents.

In certain pharmaceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development*, 2 ed.; Overseas Publ.: Amsterdam, 1996; pp 351-385; Pitman, I. H. *Medicinal Research Reviews* 1981, 1, 189-214. The prodrug forms may be active themselves, or may be those such that when metabolized after administration provide the active therapeutic agent in vivo.

Pharmaceutically acceptable salt forms may be the preferred chemical form of compounds according to the present invention for inclusion in pharmaceutical compositions according to the present invention.

Certain of the compounds, in pharmaceutical dosage form, may be used as agents for preventing a disease or condition from manifesting itself. In certain pharmaceutical dosage forms, the pro-drug form of the compounds according to the present invention may be preferred. In particular, prodrug forms which rely on $C_1$ to $C_{20}$ ester groups or amide groups (preferably a hydroxyl, free amine or substituted nitrogen group) which may be transformed into, for example, an amide or other group may be particularly useful in this context.

The present compounds or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The compounds herein are commercially available or can be synthesized. As can be appreciated by the skilled artisan, further methods of synthesizing the compounds of the formulae herein will be evident to those of ordinary skill in the art.

Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2nd. Ed., Wiley-VCH Publishers (1999); T. W. Greene and P. G. M. Wuts, *Protective Groups in Organic Synthesis,* 3rd. Ed., John Wiley and Sons (1999); L. Fieser and M. Fieser, *Fieser and Fieser's Reagents for Organic Synthesis,* John Wiley and Sons (1999); and L. Paquette, ed., *Encyclopedia of Reagents for Organic Synthesis,* John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Preferred unit dosage formulations are those containing a daily dose or unit, daily sub-dose, as hereinabove recited, or an appropriate fraction thereof, of the administered ingredient.

The dosage regimen for treating a disorder or a disease with the angiogenesis inhibiting compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject will depend on a number of factors, such as the mode of administration, the nature of the condition being treated, the body weight of the subject being treated and the judgment of the prescribing physician.

The amount of compound included within therapeutically active formulations according to the present invention is an effective amount for treating the infection or condition. In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. The dosage of the compound will depend on the condition being treated, the particular compound, and other clinical factors such as weight and condition of the patient and the route of administration of the compound. It is to be understood that the present invention has application for both human and veterinary use.

For oral administration to humans, a dosage of between approximately 0.1 to 100 mg/kg/day, preferably between approximately 1 and 100 mg/kg/day, is generally sufficient.

Where drug delivery is systemic rather than topical, this dosage range generally produces effective blood level concentrations of active compound ranging from less than about 0.04 to about 400 micrograms/cc or more of blood in the patient.

The compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In certain embodiments, the compound is administered once daily, in other embodiments, the compound is administered twice daily; in yet other embodiments, the compound is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compounds of the invention can be used to treat diseases and disease conditions that are acute, and may also be used for treatment of chronic conditions. In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

Still other objects, features, and attendant advantages of the present invention will become apparent to those skilled in the art from a reading of the preceding detailed description of embodiments constructed in accordance therewith, taken in conjunction with the accompanying drawings.

The invention also provides a pharmaceutical pack or kit comprising one or more containers filled with one or more of the ingredients of the pharmaceutical compositions of the invention. Associated with such containers) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed on conjunction with other therapeutic compounds.

The invention also provides kits for treatment or prevention of a disease or disorder (or symptoms) thereof associated with angiogenesis. In one embodiment, the kit includes an effective amount of an angiogenesis-inhibiting compound in unit dosage form, together with instructions for administering the angiogenesis-inhibiting compound to a subject suffering from or susceptible to a disease or disorder or symptoms thereof associated with angiogenesis, wherein the effective amount of an angiogenesis-inhibiting compound is less than 500 mg of the compound. In preferred embodiments, the kit comprises a sterile container which contains the angiogenesis-inhibiting compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the angiogenesis-inhibiting compound for treatment of a disease or disorder or symptoms thereof associated with angiogenesis; in preferred embodiments, the instructions include at least one of the following: description of the angiogenesis-inhibiting compound; dosage schedule and administration for treatment of a disease or disorder or symptoms thereof associated with angiogenesis; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention will be further described in the following examples. It should be understood that these examples are for illustrative purposes only and are not to be construed as limiting this invention in any manner.

EXAMPLES

Materials and Methods

Library Construction.

32,000 FDA drug approvals obtained by Freedom of Information Act requests were condensed to 3,400 unique drug formulations. Drugs were purchased from Sigma, Spectrum Chemicals, MP Biomedicals, The Johns Hopkins Hospital pharmacy, Biomol, and Tocris. 10 mM stock solutions were made using DMSO, water, or ethanol as solvents. Drugs were arrayed in 96-well plates and screened at a final concentration of 10 µM. Cells were incubated with drug for 36 h and proliferation was measured by pulsing with 1 µCi [$^3$H]-thymidine for 8 h followed by absorption onto glass filters and scintillation counting.

Statistical Analysis.

$IC_{50}$ measurements were carried out in triplicate, and analyzed using four parameter logarithmic analysis. Values are presented+/−the standard error of the mean. P-values were calculated using the Student's T-test.

Semi-Quantitative RT-PCR.

RNA from subconfluent proliferating HUVEC ($1\times10^6$) cells was prepared using a commercial kit (Roche) and 1µ of total RNA was used in the reverse transcription reaction (Superscript II, Invitrogen). cDNA was amplified by incorporating equal amounts of gene specific primers and Taq polymerase (Promega). 15 µl of this reaction was visualized on a 1% agarose gel containing 1:40,000 ethidium bromide.

IMPDH-1 and -2 siRNA knockdown. pLVV-H1 lentivirus vector was a modified version based on our previous pFUP-U6 lentivirus vector (Pan, F., Ye, Z., Cheng, L. & Liu, J. O. (2004) *J. Biol. Biol. Chem.* 279, 14477-14480). It was named double-copy design of siRNA lentivirus vector. Among the features of the new vector are, (1) the vector contains an internal marker EGFP under the control of CMV promoter; (2) a cassette containing HI promoter was cloned in the 3' U3 region of pFUP. During reverse transcription, the U3 region of the 5' LTR is synthesized by using its 3' homologue as a template, which results in a duplication of the siRNA cassette in the provirus integrated in the genome of transduced cells. For the RNA interference of IMPDH, oligos were designed and tested for three different regions of each IMPDH isoform. The best one was chosen. The oligonucleotide sequences for shRNA knockdown are as follows. For IMPDH-1, Sense: 5'-CTATCTrCAGTGGTC-TrACttcaagagaGTAAGACCACTGAAGATAGTTTTTT-3' (The first 19 nucleotides correspond to 544-562 of human IMPDH-1 cDNA (NM_00883.2), which is followed by a 9-nucleotide linker (small letters), the complementary sequence and five T's). Antisense: 5'-AAAAAACTATCT-TCAGTGGTCTTACtctcttgaaGTAAGACCACTGAAGA-TAGGGCC-3'.

For IMPDH-2, Sense: 5' GATGATGAGCTTGTGGC-CAttcaagagaTGGCCACAAGCTCATCATCTTTTTT-3' (The first 19 nucleotides correspond to 683-701 of human IMPDH-2 cDNA (BC006124.1)). Antisense: 5'-AAAAAAGATGATGAGCTTGTGGCCAtctcttgaaTG-GCCACAAGCTCATCATCGGCC-3'.

293T cell line was cultured in DMEM medium supplemented with 10% FBS. Recombinant lentiviruses were produced by transient transfection of 293T cells as follows. Briefly, subconfluent 293T cells (each well of 6-well plate) were cotransfected with 2 µg of lentivirus vector, 1.5 µg of pCMV-AR8.91, and 0.5 µg of pMD2G-VSVG by lipofectamine 2000. Supernatant containing the recombinant lentivirus was collected at 24 h and 48 h post-transfection.

For transduction, HUVEC were plated on 6-well plates ($8\times10^5$ cells/well) and incubated at 37° C. for 12 h before medium containing recombinant lentivirus was added. Following 24 h incubation, the cells were re-transduced one more time. Five days later the cells were harvested and analyzed by RT-PCR, Western blotting and cell cycle analysis.

In Vivo Angiogenesis.

Female C57BL/6NCr 5-week old, 25-30 g mice were purchased from NCI and treated in accordance with Johns Hopkins ACUC procedures. In all animal experiments the MPA prodrug mycophenolate mofetil i.v. formulation (Roche) was used. Mice were pretreated with drug for three days and then implanted with 0.5 mL of Matrigel (BD Biosciences) containing 100 ng/mL VEGF and 150 ng/mL bFGF. Drug treatment was continued daily for 10 days, mice were sacrificed, and plugs were harvested, fixed in neutral buffered formalin, and processed for histology using MAS-trichrome staining. The entire Matrigel plug was photographed at 100× and erythrocyte-filled blood vessels were counted per field.

Renal Cell Tumor Model.

Female BALB/C 5-6 week old, 25-30 g mice were purchased from NCI. Logarithmically growing RENCA cells ($5 \times 10^5$) in 50 µl, 50% PBS, 50% Matrigel were injected into the renal subcapsule through an incision in the left flank (Drevs, J., Hofmann, I., Hugenschmidt, H., Wittig, C, Madjar, H., Muller, M., Wood, J., Martiny-Baron, G., Unger, C. & Marme, D. (2000) *Cancer Res.* 60, 4819-4824). The mice were sacrificed 3.5 weeks after surgery and the primary tumors were dissected and fixed for immunohistochemistry. For CD31 analysis eight fields with the highest level of angiogenesis were selected per tumor for quantification using ImagePro Plus software (Media Cybernetics), and represented as mean percentage area occupied by CD31 positive blood vessels.

Results

FIG. 1 is table of $IC_{50}$ values for Trifluridine, Mycophenolic acid, Danazol, Asparaginase, and Itraconazole and provides $IC_{50}$ values for inhibition of different types of cells and the peak plasma level of each drug.

FIG. 2 The effects of different antifungal drugs on the proliferation of HUVEC, HFF (primary human fibroblasts), Jurkat T cells and RICO. The blank space indicated that the activity was not determined. The Values are $IC_{50}$ (in µM).

FIG. 3 is a cell cycle analysis of both endothelial cells and fibroblast cells for Fumagillin, Mycophenolic acid, Trifluridine, and Itraconazole. The effects of different drugs on the cell cycle progression of endothelial and fibroblast cells are provided.

FIG. 4 Inhibition of HUVEC by MPA and its reversal by guanine in fibroblasts.

FIG. 5 Inhibition of HUVEC by MPA and its reversal by guanine. (A) Structure of mycophenolic acid. (B) Inhibition of HUVEC proliferation by MPA as measured by [$^3$H]-thymidine incorporation. MPA inhibition (♦) is partially reversed by addition of exogenous guanine at 10 µM (■) and 20 µM (▲), however some inhibition is present even at the highest concentrations tested, 50 µM (●). (C) Inhibition of Jurkat T-cell proliferation by MPA as measured by [$^3$H]-thymidine incorporation. MPA inhibition (♦) is unaffected by addition of 10 µM exogenous guanine (■), but is completely reversed by the addition of 20 µM (▼) and 50 µM (♦) guanine, in contrast to HUVEC. (D) Cell cycle analysis of HUVEC treated with DMSO vehicle, 1 (Jvl MPA showing G1/S cell cycle arrest (E), or 1 µM MPA+50 µM guanosine (F). Addition of exogenous guanosine reverses MPA-induced G1/S cell cycle arrest.

Figure 6:
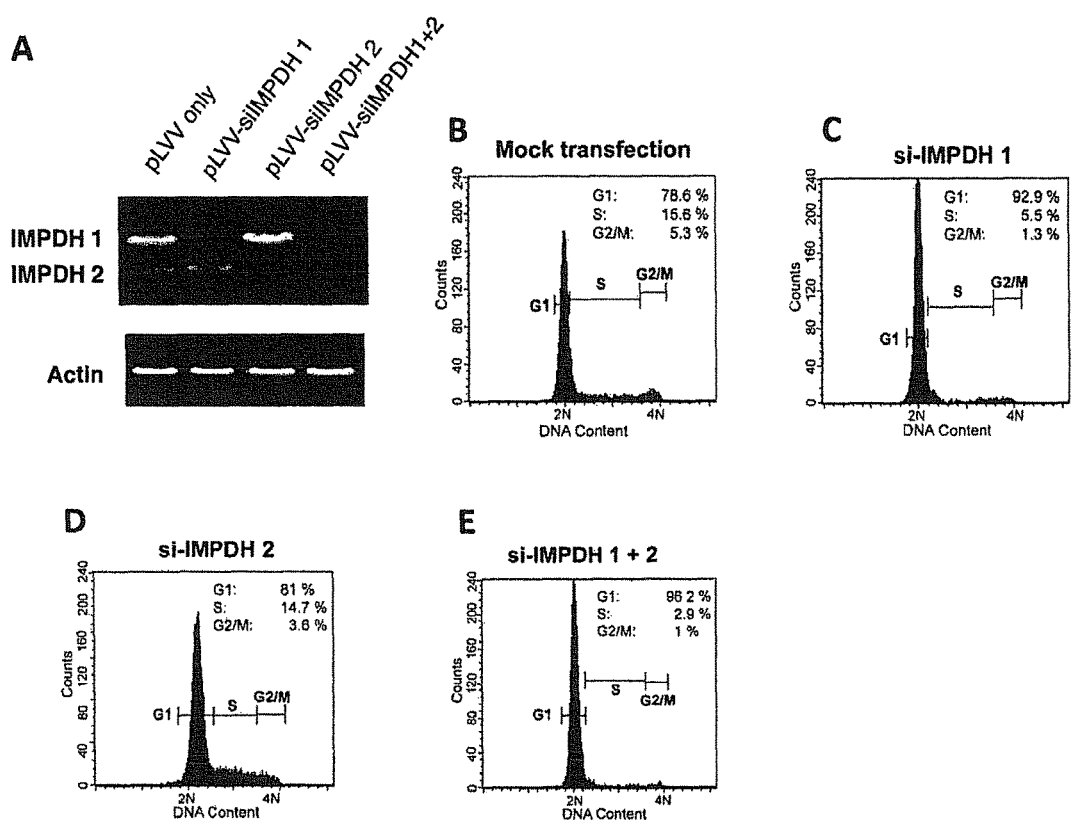
FIG. 6 shows the selective knockdown of IMPDH-1 and -2 by shRNA in HUVEC.

FIG. 6 Selective knockdown of IMPDH-1 and -2 by shRNA in HUVEC. (A) RT-PCR of IMPDH-1 and -2 knockdown in HUVEC. The IMPDH-1 and -2 shRNA vectors completely and selectively abolish IMPDH gene expression in HUVEC. (B) Cell cycle analysis of HUVEC transfected with empty vector, sh-IMPDH-1 (C), sh-IMPDH-2 (D), and sh-IMPDH-1+-2 (E) show a G1/S arrest similar to that observed with MPA treatment. This G1/S arrest is more pronounced with the shIMPDH-1 construct.

Figure 7:
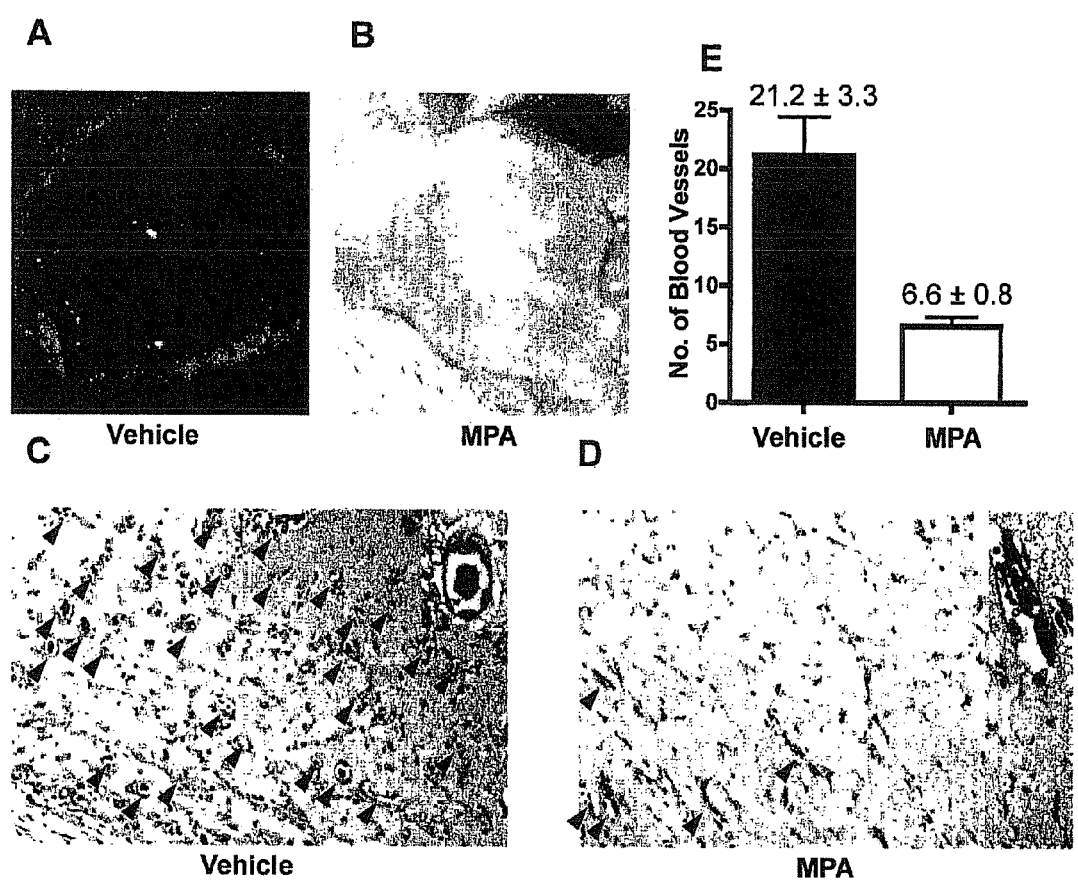
FIG. 7 illustrates the inhibition of angiogenesis in vivo.

FIG. 7 MPA inhibits angiogenesis in vivo. (A) Representative images of Matrigel plugs in mice treated with vehicle (n=7) or 60 mg/kg/day MPA (n=7) (B). (C) MAS-trichrome stain of Matrigel plug from a mouse treated with vehicle demonstrating new blood vessel formation (100× magnification, 200× inset) or MPA (60 mg/kg/day s.c.) (D) shows a 69% decrease in new blood vessel formation (p<0.002) (E).

Figure 8:
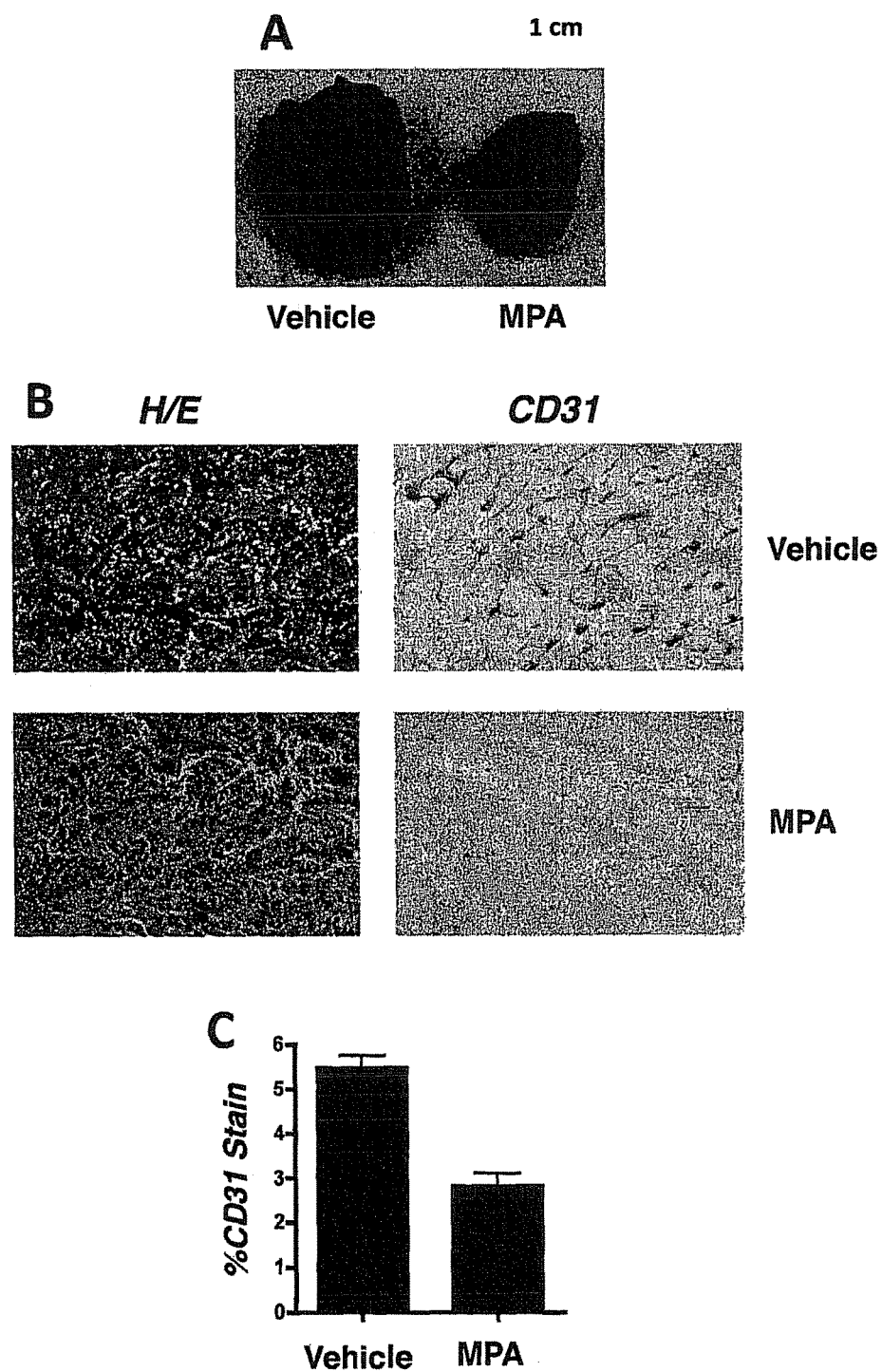
FIG. 8 illustrates the inhibition of tumor-associated angiogenesis.

FIG. 8 MPA inhibits tumor-associated angiogenesis. (A) Representative primary RENCA tumors from mice treated with vehicle (n=7), left, or 120 mg/kg/day MPA (n=8), right, showing decrease in tumor size. (B) H&E cross section (100×) of representative RENCA tumor from control mice shows extensive angiogenesis, with blood vessels highlighted by CD31 staining. In contrast, representative tumor sections from mice treated with 120 mg/kg/day MPA stained with H&E and CD31 show decreased angiogenesis compared to control. (C) Quantification of CD31 positive area per 200× microscope field shows a 49% decrease in mice treated with 120 mg/kg/day MPA (p<0.001).

A library of 1,850 FDA-approved drugs and 600 drugs that entered the clinic via approval in a foreign country or phase II clinical trials was created. To discover new angiogenesis inhibitors among known drugs, the library was screened for inhibition of human umbilical vein endothelial cells (HUVEC) using [$^3$H]-thymidine incorporation. An initial screen of the drugs at 10 µM (final concentration) revealed over 100 drugs that exhibited at least 50% inhibition. After eliminating known cytotoxic drugs such as taxol and colchicine or drugs that are restricted to topical use, several drugs remained. One of the most potent inhibitors was mycophenolic acid (MPA) (FIG. 5A). The $IC_{50}$ for MPA on HUVEC proliferation was 99.2 (±5.2) nM (FIG. 5B). Although MPA has been previously shown to inhibit endothelial cells (15, 16), the molecular basis of this inhibition remains unclear. Nor has it been shown whether MPA affected angiogenesis in vivo. A series of experiments to address these questions was thus initiated.

MPA is an immunosuppressive drug widely used to prevent rejection of transplanted organs (Lipsky, J. J. (1996) *Lancet* 348, 1357-1359). The mechanism of action in the immune system is well established-MPA inhibits de novo biosynthesis of purines in T and B lymphocytes (Allison, A. C. & Eugui, E. M. (2000) *Immunopharmacology* 47, 85-118). As the alternative nucleotide salvage pathway is absent in T and B cells, MPA was thought to specifically inhibit their proliferation by causing cell cycle arrest in the G1/S transition (Eugui, E. M., Almquist, S. J., Muller, C. D. & Allison, A. C. (1991) *Scand. J. Immunol.* 33, 161-173). Thus, a comparison of HUVEC to Jurkat T cells for sensitivity to MPA in the presence and absence of guanine was carried out. As shown in FIG. 5C, Jurkat T cells are inhibited by MPA with an $IC_{50}$ value of 128 (±6.1) nM, which is comparable to $IC_{50}$ values previously reported in human peripheral blood T and B lymphocytes (Eugui, E. M., Almquist, S. J., Muller, C. D. & Allison, A. C. (1991) *Scand. J. Immunol.* 33, 161-173). Addition of guanine at or above 20 µM rendered Jurkat T cells resistant to MPA. Similar to Jurkat T cells, inhibition of HUVEC proliferation is also reversed by guanine in a dose-dependent manner (FIG. 5B). Unlike Jurkat T cells, however, HUVECs are less sensitive to guanine, the cause of which remains unknown. Similar reversal of MPA inhibition is also seen in HUVEC and Jurkat T-cells with the addition of exogenous guanosine and deoxyguanosine (data not shown).

It has been shown that MPA causes cell cycle arrest in activated T and B lymphocytes at G1 (Laliberte, J., Yee, A., Xiong, Y. & Mitchell, B. S. (1998) *Blood* 91, 2896-2904). Therefore, the effect of MPA on endothelial cell cycle progression was examined. Treatment of HUVEC with 1 µM of MPA led to, in comparison to the control cells, an increase in the population of cells in G1 phase (81 vs. 71%) and a corresponding decrease in the population of cells in S (6.5 vs. 12%) and G2/M (12.4 vs. 17.8%) phases, indicating that MPA also causes a G1 blockade in HUVEC similar to T and B cells (FIG. 5D, E). Addition of 50 µM guanosine completely reversed the cell cycle effect of MPA in HUVEC (FIG. 5F). Together, these results strongly suggest that blockade of purine biosynthesis is responsible for the inhibition of HUVEC by MPA, similar to T and B cells.

The molecular target for MPA in T and B cells has been unambiguously established as inosine monophosphate dehydrogenase (IMPDH), which catalyzes the NAD+-dependent conversion of inosine 5'-monophosphate to xanthosine 5'-monophosphate (Allison, A. C. & Eugui, E. M. (2000) *Immunopharmacology* 47, 85-118). Two isoforms of IMPDH are known in humans, named type 1 and type 2 enzymes. Whereas IMPDH-1 is constitutively expressed, IMPDH-2 is induced in a number of tumor cell types undergoing active proliferation (Collart, F. R., Chubb, C. B., Mirkin, B. L. & Huberman, E. (1992) *Cancer Res.* 52, 5826-5828). The expression of the two isoforms in actively proliferating HUVEC was assessed using RT-PCR. It was found that IMPDH-1 is the predominantly expressed isoform in HUVEC, although IMPDH-2 rriRNA is also detected (data not shown). This expression pattern is similar to that in peripheral leukocytes but distinct from those in most other tissues in which IMPDH-2 is more abundantly expressed (Senda, M. & Natsumeda, Y. (1994) *Life Sci.* 54, 1917-1926). To determine whether inhibition of either isoform of IMPDH accounts for the effect of MPA on HUVEC, each isoform was knocked down by RNA interference. To avoid subjecting the primary HUVEC to the relatively harsh conditions of conventional transfection methods, lentiviruses were used to deliver isoform-specific shRNAs to HUVEC (Pan, F., Ye, Z., Cheng, L. & Liu, J. O. (2004) *J. Biol, Chem.* 279, 14477-14480, Lois, C, Hong, E. J., Pease, S., Brown, E. J. & Baltimore, D. (2002) *Science* 295, 868-872). Upon testing three different regions of each IMPDH cDNA, at least one shRNA construct was found that efficiently blocked the expression of either IMPDH-1 or IMPDH-2 with high specificity (FIG. 6A). Transduction of HUVEC with a mixture of lentiviruses carrying shRNAs for both IMPDH-1 and IMPDH-2 led to the knockdown of mRNA (FIG. 6A) and protein (data not shown) for both isoforms. The effects of knockdown of the two isoforms of IMPDH on the cell cycle of HUVEC were then determined. As shown in FIG. 6B-C, knockdown of IMPDH-1 is sufficient to cause a cell cycle arrest in G1. Interestingly, knockdown of IMPDH-2 appeared to cause a significant delay in S phase progression rather than a G1 blockade (FIG. 6D). Not surprisingly, knockdown of both isoforms of IMPDH also led to accumulation of HUVEC in G1 (FIG. 6E). These observations validated IMPDH-1 as the target for MPA in endothelial cells.

To test the in vivo efficacy of MPA as an anti-angiogenic inhibitor, we performed the Matrigel plug angiogenesis assay in mice using doses previously used to demonstrate immunosuppression in murine transplant models (van Leeuwen, L., Guiffre, A. K., Sewell, W. A., Vos, B. J., Rainer, S. & Atkinson, K. (1997) *Transplantation* 64, 1097-1101, Fahmy, R. G., Dass, C. R., Sun, L. Q., Chesterman, C. N. & Khachigian, L. M. (2003) *Nat. Med.* 9, 1026-1032). Matrigel plugs containing VEGF and bFGF were subcutaneously implanted into mice. The control group was treated with saline vehicle and the MPA group was treated with 60 or 120 mg/kg/day of drug. After 10 days, plugs from control mice showed extensive neovascularization that is visible both macroscopically (FIG. 7A) and microscopically (FIG. 7C). In contrast, MPA treated mice had significantly less new blood vessel formation (FIG. 7B, D). To quantify these differences we counted erythrocyte-filled blood vessels per 100x field (FIG. 7E) (Fahmy, R. G., Dass, C. R., Sun, L. Q., Chesterman, C. N. & Khachigian, L. M. (2003) *Nat. Med.* 9, 1026-1032), and observed a 69% decrease in new blood vessel formation in mice treated with MPA in comparison with vehicle control (p<0.002). Thus, MPA is capable of inhibiting angiogenesis at a therapeutically achievable dose in vivo.

Angiogenesis has been implicated in tumor growth among a number of other diseases (11). Although MPA inhibits fast-growing tumor cell lines in culture and in mouse xenograph experiments (Tressler, R. J., Garvin, L. J. & Slate, D. L. (1994) *Int. Cancer* 57, 568-573, Carter, S. B., Franklin, T. J., Jones, D. F., Leonard, B. J., Mills, S. D., Turner, R. W. & Turner, W. B. (1969) *Nature* 223, 848-850), it is unclear whether MPA also affects tumor-associated angiogenesis. We determined the efficacy of MPA in inhibiting tumor-associated angiogenesis in a murine renal cell carcinoma (RENCA) model (Salup, R. R. & Wiltrout, R. H. (1986) *Cancer Res,* 46, 3358-3363). MPA inhibited the growth of the primary tumor in a dose-dependent fashion, causing a 34% and 27% decrease in volume and weight, respectively, at 60 mg/kg/day and a 64% decrease in both volume and weight at 120 mg/kg/day (p<0.001) (FIG. 8A). The decrease in tumor growth caused by MPA at 120 mg/kg/day was accompanied by a 48% decrease in the area of CD31 positive staining blood vessels per 200x field (p<0.001). As shown in FIG. 8B, C, whereas CD31 positive blood vessels were abundant in tumors from control animals, MPA treatment at 120 mg/kg/day led to a significant reduction in CD31 positive vessels in the primary tumor. These results demonstrate that MPA is capable of decreasing tumor-induced angiogenesis in vivo.

All references cited herein, whether in print, electronic, computer readable storage media or other form, are expressly incorporated by reference in their entirety, including but not limited to, abstracts, articles, journals, publications, texts, treatises, technical data sheets, interne web sites, databases, patents, patent applications, and patent publications.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof; and other mixtures thereof; as falling within the scope of the invention. Additional asymmetric carbon atoms may be present in a substituent such as an alkyl group. All such enriched isomers, as well as racemic mixtures thereof, are intended to be included in this invention.

A number of embodiments of the invention have been described. Embodiments herein include those recited alone or in combination with other delineated embodiments herein. Nevertheless, it will be understood that various modifications may be made without departing from the spirit and scope of the invention. Accordingly, other embodiments are within the scope of the following claims.

What is claimed:

1. A method of inhibiting angiogenesis in a subject having an ocular disease or disorder comprising administering to the subject an effective amount of danazol, thereby inhibiting angiogenesis.

2. The method of claim 1, wherein danazol is provided in an amount effective for treatment of retinoblastoma, cystoid macular edema (CME), exudative age-related macular degeneration (AMD), diabetic retinopathy, diabetic macular edema, or ocular inflammatory disorders.

3. The method of claim 1, wherein the subject has a tumor in the eye or eye cancer and the administering treats the tumor.

4. The method of claim 1, wherein the subject has a disease or disorder of the retina.

5. The method of claim 1, further comprising administering an additional therapeutic agent.

6. The method of claim 5, wherein the additional therapeutic agent is an angiogenesis-inhibiting compound.

7. The method of claim 5, wherein the additional therapeutic agent is an anticancer compound.

8. The method of claim 1, wherein the administering comprises administering the compound orally, topically, parentally, intravenously, intraocularly or intramuscularly.

9. The method of claim 8, wherein the administering is carried out in a controlled and sustained release.

10. The method of claim 1, wherein the administering comprises administering the compound in a dosage of between about 0.1 and 100 mg/kg/day.

11. The method of claim 1, wherein the administering comprises administering the compound in a dosage of less than about 500 mg/day.

12. The method of claim 1, wherein the ocular disease or disorder is eye or ocular cancer.

13. The method of claim 1, wherein the ocular disease or disorder is neovascularization.

14. The method of claim 13, wherein the ocular disease or disorder is selected from the group consisting of: diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, phylectenulosis, Mycobacteria infections, Mooren's ulcer, Terrien's marginal degeneration, marginal keratolysis, scleritis, radial keratotomy, corneal graft rejection, macular edema, macular degeneration, pseudoxanthoma elasticum, chronic uveitis/vitritis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, toxoplasmosis, trauma and post-laser complications, and diseases associated with rubeosis.

15. The method of claim 14, wherein the ocular disease or disorder is diabetic retinopathy, macular edema or macular degeneration.

16. The method of claim 8, wherein the delivery is via an ocular delivery system applied to an intra-ocular lens to prevent inflammation or posterior capsular opacification.

17. The method of claim 8, wherein delivery is via an ocular delivery system that is inserted directly into the vitreous, under the retina, or onto the sclera.

18. The method of claim 17, wherein inserting is by injecting the system or surgically implanting the system or a sustained release drug delivery system.

19. The method of claim 1, wherein the subject is human.

* * * * *

UNITED STATES PATENT AND TRADEMARK OFFICE
CERTIFICATE OF CORRECTION

PATENT NO. : 9,642,865 B2
APPLICATION NO. : 14/530398
DATED : May 9, 2017
INVENTOR(S) : Jun Liu et al.

Page 1 of 1

It is certified that error appears in the above-identified patent and that said Letters Patent is hereby corrected as shown below:

In the Specification

On Column 1, please replace Lines 17-22 with the following:
STATEMENT OF GOVERNMENTAL INTEREST
This invention was made with government support under grant number CA078743, awarded by the National Institutes of Health and grant number W81XWH-04-1-0318, awarded by ARMY/MRMC. The government has certain rights in the invention.

Signed and Sealed this
Sixth Day of November, 2018

Andrei Iancu
*Director of the United States Patent and Trademark Office*